US011648172B2

(12) United States Patent
Chase et al.

(10) Patent No.: US 11,648,172 B2
(45) Date of Patent: May 16, 2023

(54) COMPRESSION GARMENT SYSTEMS

(71) Applicant: TACTILE SYSTEMS TECHNOLOGY, INC., Minneapolis, MN (US)

(72) Inventors: Daniel G. Chase, Menomonie, WI (US); Mark R. Riley, St. Paul, MN (US); Gregory Robert Straka, Shoreview, MN (US)

(73) Assignee: TACTILE SYSTEMS TECHNOLOGY, INC., Minneapolis, MN (US)

( * ) Notice: Subject to any disclaimer, the term of this patent is extended or adjusted under 35 U.S.C. 154(b) by 769 days.

(21) Appl. No.: 16/182,337

(22) Filed: Nov. 6, 2018

(65) Prior Publication Data

US 2019/0133872 A1    May 9, 2019

Related U.S. Application Data

(60) Provisional application No. 62/582,281, filed on Nov. 6, 2017.

(51) Int. Cl.
*A61H 9/00* (2006.01)
*A61F 13/00* (2006.01)
*A61F 13/08* (2006.01)

(52) U.S. Cl.
CPC ..... *A61H 9/0078* (2013.01); *A61F 13/00051* (2013.01); *A61F 13/08* (2013.01);
(Continued)

(58) Field of Classification Search
CPC ...... A61H 9/0078; A61H 9/0092; A61H 9/00; A61H 9/0085; A61H 9/005;
(Continued)

(56) References Cited

U.S. PATENT DOCUMENTS 1,309,783 A    7/1919   Slawin
1,608,239 A   11/1926   Rosett
(Continued)

FOREIGN PATENT DOCUMENTS

CN    102652009 A    8/2012
CN    107272759 A    7/2017
(Continued)

OTHER PUBLICATIONS

U.S. Appl. No. 29/666,140, filed Oct. 10, 2018, Wennen et al.
(Continued)

*Primary Examiner* — Justine R Yu
*Assistant Examiner* — Kelsey E Baller
(74) *Attorney, Agent, or Firm* — Mueting Raasch Group

(57) ABSTRACT

Compression garment systems and methods may deliver fluid to one or more fluid cells using a target pressure and an adjustable manifold pressure that may be adjusted to, for example, deliver an amount of fluid to the one or more fluid cells to achieve the desired target pressure. Further, the compression garment systems and methods may provide a graphical user interface depicting a human-shaped graphical element and a compression therapy graphical indication about the human-shaped graphical element. The compression therapy graphical indication may indicate, or show, where on the human-shaped graphical element the compression therapy may be delivered to. Still further, the compression garment systems and methods may include or use a communication interface to determine or identify a compression garment to be used therewith. The identity of the compression garment can be used to configure compression therapy for the compression garment.

17 Claims, 23 Drawing Sheets

(52) U.S. Cl.
CPC ............ *A61H 2201/1604* (2013.01); *A61H 2201/164* (2013.01); *A61H 2201/165* (2013.01); *A61H 2201/1619* (2013.01); *A61H 2201/1635* (2013.01); *A61H 2201/5025* (2013.01); *A61H 2201/5046* (2013.01); *A61H 2201/5071* (2013.01); *A61H 2201/5097* (2013.01)

(58) Field of Classification Search
CPC .... A61H 2201/1604; A61H 2201/1619; A61H 2201/1635; A61H 2201/164; A61H 2201/165; A61H 2201/5046; A61H 2201/5071; A61H 2201/5097; A61H 2201/5025; A61H 2205/06; A61H 2205/08; A61H 2205/10; A61F 13/08; A61F 13/00051
See application file for complete search history.

(56) References Cited

U.S. PATENT DOCUMENTS

| | | |
|---|---|---|
| 1,795,893 A | 3/1931 | Rosett |
| D113,429 S | 2/1939 | Mehl |
| 2,823,668 A | 2/1958 | Van Court et al. |
| 3,094,118 A | 6/1963 | De Besme |
| 3,159,160 A | 12/1964 | Ullom |
| 3,397,688 A | 8/1968 | Gottfried |
| 3,606,890 A | 9/1971 | Gibert |
| 3,659,593 A | 5/1972 | Vail |
| D224,282 S | 7/1972 | Candela |
| D253,976 S | 1/1980 | Davidson |
| 4,210,147 A | 7/1980 | Nestor et al. |
| 4,317,239 A | 3/1982 | Bryska |
| D293,932 S | 1/1988 | Ramseyer |
| 4,765,338 A | 8/1988 | Turner et al. |
| 4,787,372 A | 11/1988 | Ramseyer |
| 4,884,295 A | 12/1989 | Cox |
| D307,054 S | 4/1990 | Johnson, Jr. |
| 4,920,963 A | 5/1990 | Brader |
| 4,937,880 A | 7/1990 | Beard |
| 4,940,045 A | 7/1990 | Cromartie |
| D311,261 S | 10/1990 | Avey |
| 5,014,365 A | 5/1991 | Schulz |
| 5,014,681 A | 5/1991 | Heeman et al. |
| 5,031,246 A | 7/1991 | Kronenberger |
| 5,033,461 A | 7/1991 | Young et al. |
| 5,038,765 A | 8/1991 | Young et al. |
| 5,039,247 A | 8/1991 | Young et al. |
| 5,046,490 A | 9/1991 | Young et al. |
| 5,083,553 A | 1/1992 | Stevenson et al. |
| D331,300 S | 11/1992 | Fountain |
| 5,188,587 A | 2/1993 | McGuire et al. |
| 5,205,815 A | 4/1993 | Saunders |
| 5,215,517 A | 6/1993 | Stevenson et al. |
| 5,314,455 A | 5/1994 | Johnson, Jr. et al. |
| 5,334,134 A | 8/1994 | Saunders |
| 5,349,702 A | 9/1994 | Runckel |
| 5,383,844 A | 1/1995 | Munoz et al. |
| 5,399,150 A | 3/1995 | Saunders |
| 5,407,420 A | 4/1995 | Bastyr et al. |
| 5,449,379 A | 9/1995 | Hadtke |
| 5,466,250 A | 11/1995 | Johnson, Jr. et al. |
| 5,536,246 A | 7/1996 | Saunders |
| 5,628,725 A | 5/1997 | Ostergard |
| D383,204 S | 9/1997 | Lomas |
| 5,697,962 A | 12/1997 | Brink et al. |
| D389,584 S | 1/1998 | Leventhal et al. |
| 5,733,321 A | 3/1998 | Brink |
| 5,741,220 A | 4/1998 | Brink |
| 5,792,082 A | 8/1998 | Yamanaka |
| 5,848,982 A | 12/1998 | Hoshino et al. |
| 5,921,946 A | 7/1999 | Tillinghast et al. |
| 5,928,262 A | 7/1999 | Harber |
| 5,976,099 A | 11/1999 | Kellogg |
| 5,997,465 A | 12/1999 | Savage et al. |
| 6,030,412 A | 2/2000 | Klatz et al. |
| 6,039,704 A | 3/2000 | Domenighini |
| 6,110,133 A | 8/2000 | Ritts |
| 6,126,683 A | 10/2000 | Momtahemi |
| 6,179,796 B1 | 1/2001 | Waldridge |
| 6,338,723 B1 | 1/2002 | Carpenter et al. |
| 6,436,064 B1 | 8/2002 | Kloecker |
| 6,551,280 B1 | 4/2003 | Knighton et al. |
| 6,592,535 B2 | 7/2003 | Ravikumar |
| 6,645,165 B2 | 11/2003 | Waldridge et al. |
| 6,860,862 B2 | 3/2005 | Waldridge et al. |
| 6,966,884 B2 | 11/2005 | Waldridge et al. |
| D522,179 S | 5/2006 | Wright |
| 7,044,924 B1 | 5/2006 | Roth et al. |
| D532,511 S | 11/2006 | Amarasinghe |
| 7,156,818 B2 | 1/2007 | Salmon et al. |
| D538,509 S | 3/2007 | Silverman |
| D554,225 S | 10/2007 | Peterson |
| 7,311,687 B2 | 12/2007 | Hoffmeier et al. |
| 7,396,345 B2 | 7/2008 | Knighton et al. |
| D578,652 S | 10/2008 | Tabron et al. |
| D587,408 S | 2/2009 | Leonardi |
| D596,805 S | 7/2009 | Leonardi |
| 7,563,236 B2 | 7/2009 | Kazmierczak et al. |
| 7,591,050 B2 | 9/2009 | Hammerslag |
| D604,910 S | 11/2009 | Smaller |
| 7,631,382 B2 | 12/2009 | Dibenedetto et al. |
| 7,691,084 B2 | 4/2010 | Knighton et al. |
| 7,698,909 B2 | 4/2010 | Hannula et al. |
| 7,741,966 B2 | 6/2010 | Bonnefin et al. |
| 7,749,181 B2 | 7/2010 | Simmons et al. |
| 7,771,376 B2 | 8/2010 | Roth et al. |
| D624,705 S | 9/2010 | Wright |
| 7,857,777 B2 | 12/2010 | Larson et al. |
| 7,887,501 B2 | 2/2011 | Riordan et al. |
| 7,909,786 B2 | 3/2011 | Bonnefin et al. |
| 7,947,003 B2 | 5/2011 | Bonnefin et al. |
| 7,959,591 B2 | 6/2011 | Powers et al. |
| 7,967,765 B2 | 6/2011 | Nathanson |
| 8,046,937 B2 | 11/2011 | Beers et al. |
| 8,075,507 B2 | 12/2011 | Linnane et al. |
| 8,096,964 B1 | 1/2012 | Bruehwiler et al. |
| 8,147,438 B2 | 4/2012 | Livolsi et al. |
| 8,182,437 B2 | 5/2012 | Gasbarro et al. |
| 8,202,236 B2 | 6/2012 | Gasbarro |
| 8,226,698 B2 | 7/2012 | Edelman et al. |
| D668,000 S | 9/2012 | Folkesson et al. |
| 8,273,114 B2 | 9/2012 | Wasowski |
| 8,381,362 B2 | 2/2013 | Hammerslag et al. |
| D686,738 S | 7/2013 | Tabron et al. |
| 8,517,963 B2 | 8/2013 | Larson et al. |
| 8,517,965 B2 | 8/2013 | Doty et al. |
| D690,487 S | 10/2013 | Lee |
| D692,186 S | 10/2013 | Phillips |
| 8,574,180 B2 | 11/2013 | Tabron et al. |
| 8,591,440 B2 | 11/2013 | Logue et al. |
| D694,957 S | 12/2013 | Barker et al. |
| 8,597,219 B2 | 12/2013 | Hargrave et al. |
| D698,031 S | 1/2014 | Viner et al. |
| 8,636,679 B2 | 1/2014 | Linnane et al. |
| 8,641,654 B2 | 2/2014 | Verkade et al. |
| 8,667,613 B2 | 3/2014 | Blakely et al. |
| D706,990 S | 6/2014 | Martin |
| 8,764,689 B2 | 7/2014 | Toth |
| D714,022 S | 9/2014 | Mong et al. |
| D729,457 S | 5/2015 | Kim |
| 9,027,408 B2 | 5/2015 | Toth et al. |
| D733,361 S | 6/2015 | Welborn |
| 9,044,372 B2 | 6/2015 | Wild et al. |
| 9,114,053 B2 | 8/2015 | Wright et al. |
| 9,114,257 B2 | 8/2015 | Helfer et al. |
| D740,934 S | 10/2015 | Formica et al. |
| D743,110 S | 11/2015 | Welborn |
| D744,202 S | 12/2015 | Brown |
| 9,248,074 B2 | 2/2016 | Toth |
| D750,843 S | 3/2016 | Welborn |
| D751,211 S | 3/2016 | Moreland |
| D751,768 S | 3/2016 | Kim |

(56) References Cited

U.S. PATENT DOCUMENTS

| | | | |
|---|---|---|---|
| 9,278,043 B2 | 3/2016 | Tabron et al. | |
| 9,295,605 B2 | 3/2016 | Yurko et al. | |
| 9,320,307 B2 | 4/2016 | Berns et al. | |
| D767,115 S | 9/2016 | Mingo | |
| 9,463,135 B2 | 10/2016 | Tabron et al. | |
| D770,730 S | 11/2016 | Borovicka | |
| D777,380 S | 1/2017 | Win | |
| 9,539,166 B2 | 1/2017 | Wild et al. | |
| D782,030 S | 3/2017 | Prentice et al. | |
| 9,591,884 B2 | 3/2017 | Jurga et al. | |
| D784,515 S | 4/2017 | Prentice et al. | |
| D791,441 S | 7/2017 | Van Sisseren | |
| 9,737,238 B2 | 8/2017 | Wright et al. | |
| D797,277 S | 9/2017 | Blanch et al. | |
| D810,277 S | 2/2018 | Amarasinghe et al. | |
| 9,889,063 B2 | 2/2018 | Wright et al. | |
| 10,022,289 B2 | 7/2018 | Ajiki | |
| 10,071,012 B2 | 9/2018 | Larson et al. | |
| D831,220 S | 10/2018 | Chase et al. | |
| 10,092,250 B2 | 10/2018 | Tucker et al. | |
| D833,682 S | 11/2018 | Greenblat et al. | |
| D834,179 S | 11/2018 | Smith | |
| D834,208 S | 11/2018 | Wennen et al. | |
| D837,971 S | 1/2019 | Prentice et al. | |
| D839,484 S | 1/2019 | Chase et al. | |
| 10,195,102 B2 | 2/2019 | Wright et al. | |
| D848,625 S | 5/2019 | Chase et al. | |
| D849,254 S | 5/2019 | Chase et al. | |
| 10,292,894 B2 | 5/2019 | Wright et al. | |
| 10,470,967 B2 | 11/2019 | Wright | |
| D868,957 S | 12/2019 | Chase et al. | |
| D870,297 S | 12/2019 | Chase et al. | |
| 10,492,974 B2 | 12/2019 | Chase et al. | |
| D873,497 S | 1/2020 | Chase et al. | |
| D877,459 S | 3/2020 | Chase et al. | |
| 10,736,805 B2* | 8/2020 | Johnson | A61B 5/022 |
| 2003/0032905 A1 | 2/2003 | Waldridge et al. | |
| 2003/0199922 A1 | 10/2003 | Buckman | |
| 2005/0060789 A1 | 3/2005 | Waldman | |
| 2005/0148918 A1 | 7/2005 | Nathanson | |
| 2005/0154336 A1 | 7/2005 | Kloecker et al. | |
| 2006/0000478 A1 | 1/2006 | Taylor | |
| 2006/0085881 A1 | 4/2006 | Gellis et al. | |
| 2006/0130213 A1 | 6/2006 | Mickle | |
| 2006/0156517 A1 | 7/2006 | Hammerslag et al. | |
| 2006/0200057 A1 | 9/2006 | Sterling | |
| 2007/0049863 A1 | 3/2007 | Jahns et al. | |
| 2007/0088234 A1 | 4/2007 | Tseng | |
| 2007/0161932 A1 | 7/2007 | Pick et al. | |
| 2007/0169378 A1 | 7/2007 | Sodeberg et al. | |
| 2008/0243010 A1* | 10/2008 | Kulik | A61B 5/02233 600/499 |
| 2009/0178176 A1 | 7/2009 | Rowe et al. | |
| 2009/0254014 A1 | 10/2009 | Son | |
| 2009/0299259 A1 | 12/2009 | Cumming et al. | |
| 2010/0031963 A1 | 2/2010 | Lee et al. | |
| 2010/0228171 A1 | 9/2010 | Waldridge | |
| 2010/0016775 A1 | 10/2010 | Cumming et al. | |
| 2011/0009793 A1 | 1/2011 | Lucero et al. | |
| 2011/0087142 A1 | 4/2011 | Ravikumar et al. | |
| 2011/0087143 A1 | 4/2011 | Bobey et al. | |
| 2011/0172579 A1 | 7/2011 | Chiu et al. | |
| 2011/0178447 A1 | 7/2011 | Helfer et al. | |
| 2011/0185482 A1 | 8/2011 | Godfrey et al. | |
| 2011/0257463 A1 | 10/2011 | Nour et al. | |
| 2012/0004587 A1 | 1/2012 | Nickel et al. | |
| 2012/0023648 A1 | 2/2012 | Dainese | |
| 2012/0116291 A1 | 5/2012 | Mogi | |
| 2012/0150086 A1 | 6/2012 | Cohen | |
| 2012/0179084 A1 | 7/2012 | Lipshaw et al. | |
| 2012/0296252 A1 | 11/2012 | Cumming et al. | |
| 2013/0012847 A1 | 1/2013 | Lowe et al. | |
| 2013/0012856 A1 | 1/2013 | Hammerslag et al. | |
| 2013/0079854 A1 | 3/2013 | Wasowski | |
| 2013/0152930 A1 | 6/2013 | Votel et al. | |
| 2013/0197413 A1 | 8/2013 | Hoffmeier et al. | |
| 2013/0211300 A1 | 8/2013 | Verkade et al. | |
| 2013/0269219 A1 | 10/2013 | Burns et al. | |
| 2013/0345612 A1 | 12/2013 | Bannister et al. | |
| 2014/0018752 A1 | 1/2014 | Shuler | |
| 2014/0033402 A1 | 2/2014 | Donnadieu et al. | |
| 2014/0094728 A1 | 4/2014 | Soderberg et al. | |
| 2014/0123449 A1 | 5/2014 | Soderberg et al. | |
| 2014/0128787 A1 | 5/2014 | Linnane et al. | |
| 2014/0130803 A1 | 5/2014 | Feldhahn et al. | |
| 2014/0222121 A1 | 8/2014 | Spence et al. | |
| 2014/0276271 A1 | 9/2014 | Stryker | |
| 2014/0276290 A1* | 9/2014 | Mansur, Jr. | A61H 9/0078 601/152 |
| 2015/0119775 A1 | 4/2015 | Gildersleeve et al. | |
| 2015/0157484 A1 | 6/2015 | Ex-Lubeskie et al. | |
| 2015/0224011 A1 | 8/2015 | Scott | |
| 2015/0224012 A1 | 8/2015 | Wright | |
| 2015/0297437 A1 | 10/2015 | Neuenhahn et al. | |
| 2016/0022528 A1 | 1/2016 | Wyatt et al. | |
| 2016/0082319 A1 | 3/2016 | Macri et al. | |
| 2016/0058644 A1 | 4/2016 | Cheatham, III et al. | |
| 2016/0166464 A1 | 6/2016 | Douglas et al. | |
| 2016/0193100 A1 | 7/2016 | Toth | |
| 2016/0213548 A1 | 7/2016 | William | |
| 2016/0220808 A1 | 8/2016 | Hyde et al. | |
| 2016/0361224 A1* | 12/2016 | Ramakrishna | A61H 9/0078 |
| 2017/0020770 A1 | 1/2017 | Tabron et al. | |
| 2017/0095393 A1 | 4/2017 | Wennen et al. | |
| 2017/0095394 A1 | 4/2017 | Wennen et al. | |
| 2017/0095395 A1 | 4/2017 | Wennen et al. | |
| 2017/0095396 A1 | 4/2017 | Chase et al. | |
| 2017/0105893 A1 | 4/2017 | Kim et al. | |
| 2017/0105894 A1* | 4/2017 | Newton | A61H 23/04 |
| 2017/0112709 A1 | 4/2017 | Wild et al. | |
| 2017/0209332 A1 | 7/2017 | Chase et al. | |
| 2017/0258672 A1 | 9/2017 | Wennen et al. | |
| 2017/0303607 A1 | 10/2017 | Iser et al. | |
| 2017/0311847 A1 | 11/2017 | Wright et al. | |
| 2017/0312161 A1* | 11/2017 | Johnson | A61F 5/0123 |
| 2018/0049939 A1* | 2/2018 | Bobey | A61H 23/0218 |
| 2018/0098707 A1* | 4/2018 | Salamon | A61B 5/4836 |
| 2019/0015295 A1* | 1/2019 | Marton | A61H 23/0254 |
| 2019/0133873 A1 | 5/2019 | Chase et al. | |
| 2019/0167509 A1 | 6/2019 | Wright et al. | |
| 2019/0290220 A9 | 9/2019 | Tucker et al. | |
| 2020/0038284 A1 | 2/2020 | Wright et al. | |
| 2020/0113773 A1* | 4/2020 | Ramanan | A61H 9/0092 |
| 2020/0315905 A1* | 10/2020 | Rizzo | A61H 11/00 |

FOREIGN PATENT DOCUMENTS

| | | |
|---|---|---|
| EP | 2168555 A1 | 3/2010 |
| EP | 2 226 044 A2 | 9/2010 |
| EP | 2 462 905 B1 | 11/2013 |
| EP | 2671560 A1 | 12/2013 |
| EP | 1 703 871 B1 | 5/2015 |
| EP | 2 339 998 B1 | 5/2015 |
| EP | 2 613 745 B1 | 6/2015 |
| EP | 2 248 493 B1 | 9/2015 |
| FR | 2 624 003 A1 | 11/1988 |
| FR | 2 939 642 A1 | 6/2010 |
| GB | 699152 | 10/1953 |
| WO | WO 96/12521 A1 | 5/1995 |
| WO | WO 03/041621 A1 | 5/2003 |
| WO | WO 2007/014242 A1 | 2/2007 |
| WO | WO 2008/033963 A2 | 3/2008 |
| WO | WO 2014/151902 A1 | 9/2014 |
| WO | WO 2014/159706 A2 | 10/2014 |
| WO | WO 2015/038822 A1 | 3/2015 |
| WO | WO 2015/050897 A1 | 4/2015 |
| WO | WO 2015/117132 A1 | 8/2015 |
| WO | WO 2015/200203 A1 | 12/2015 |

OTHER PUBLICATIONS

U.S. Appl. No. 29/690,968, filed Feb. 13, 2019, Chase et al.
International Patent Application No. PCT/US2016/055275, filed

(56) References Cited

OTHER PUBLICATIONS

Oct. 4, 2016; International Search Report/ Written Opinion dated Dec. 20, 2016; 15 pages.
International Patent Application No. PCT/US2016/055272, filed Oct. 4, 2016; International Search Report / Written Opinion dated Dec. 20, 2016; 16 pages.
Patent Application No. PCT/US2017/014249, filed Jan. 20, 2017; International Search Report / Written Opinion dated Apr. 4, 2017; 14 pages.
International Patent Application No. PCT/US2016/055275, filed Oct. 4, 2016; International Preliminary Report on Patentability dated Apr. 19, 2018; 9 pages.
PCT/US2016/055272, filed Oct. 4, 2016; International Preliminary Report on Patentability, dated Apr. 19, 2018; 10 pages.
International Patent Application No. PCT/US2018/059468, filed Nov. 6, 2018; International Search Report / Written Opinion dated Mar. 14, 2019; 14 pages.
International Patent Application No. PCT/US2018/059467, filed Nov. 6, 2018; International Search Report / Written Opinion dated Feb. 5, 2019; 16 pages.

* cited by examiner

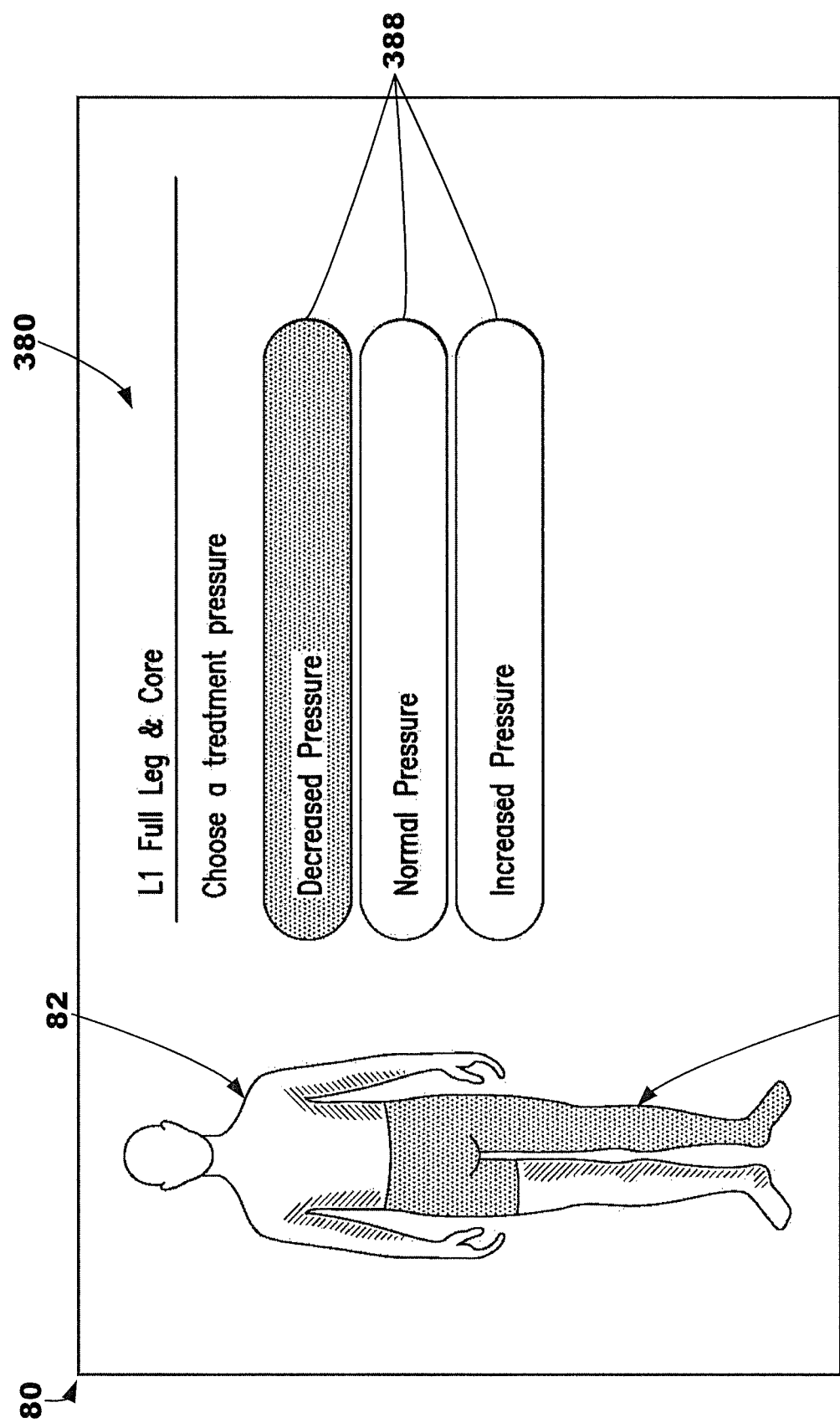

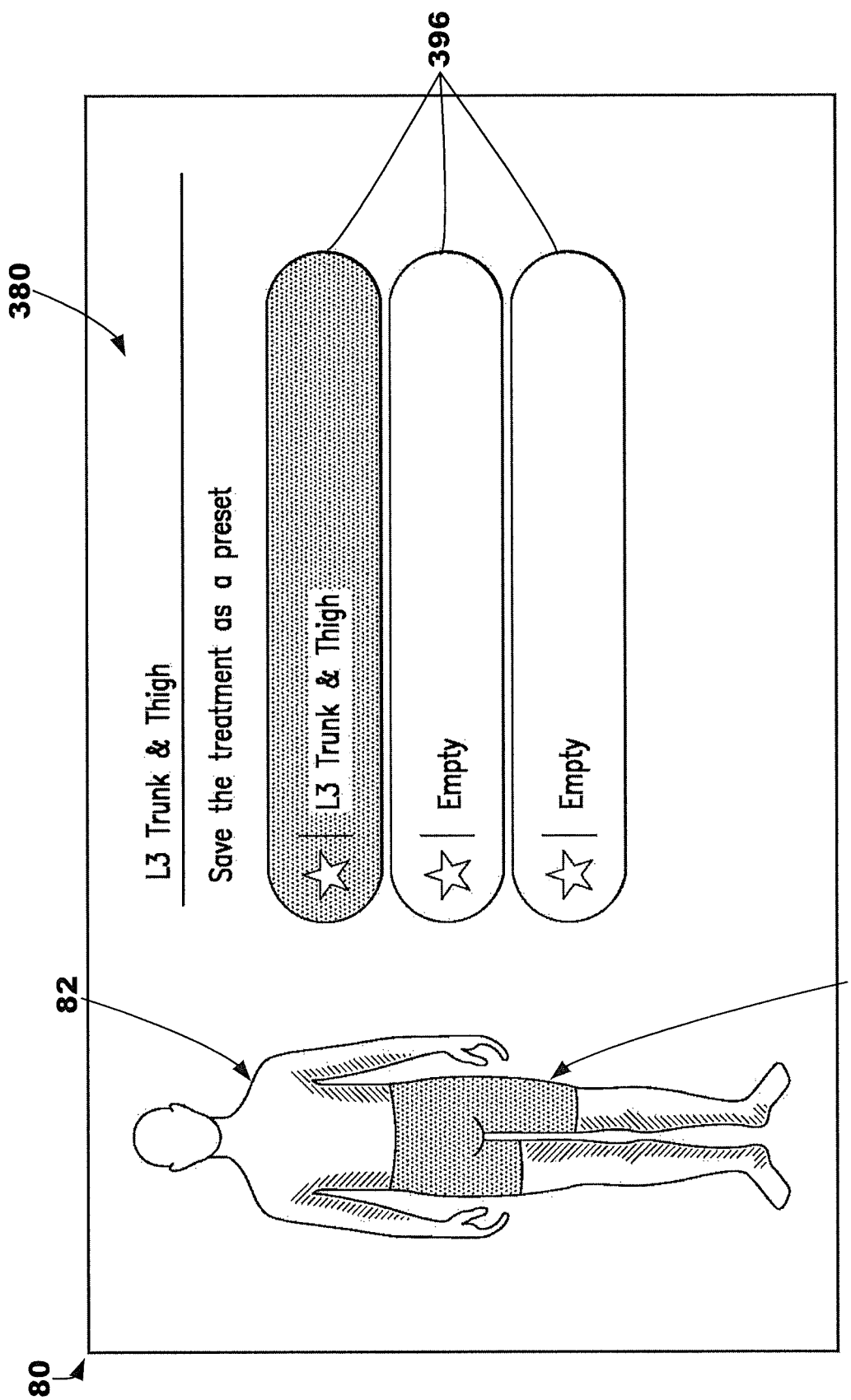

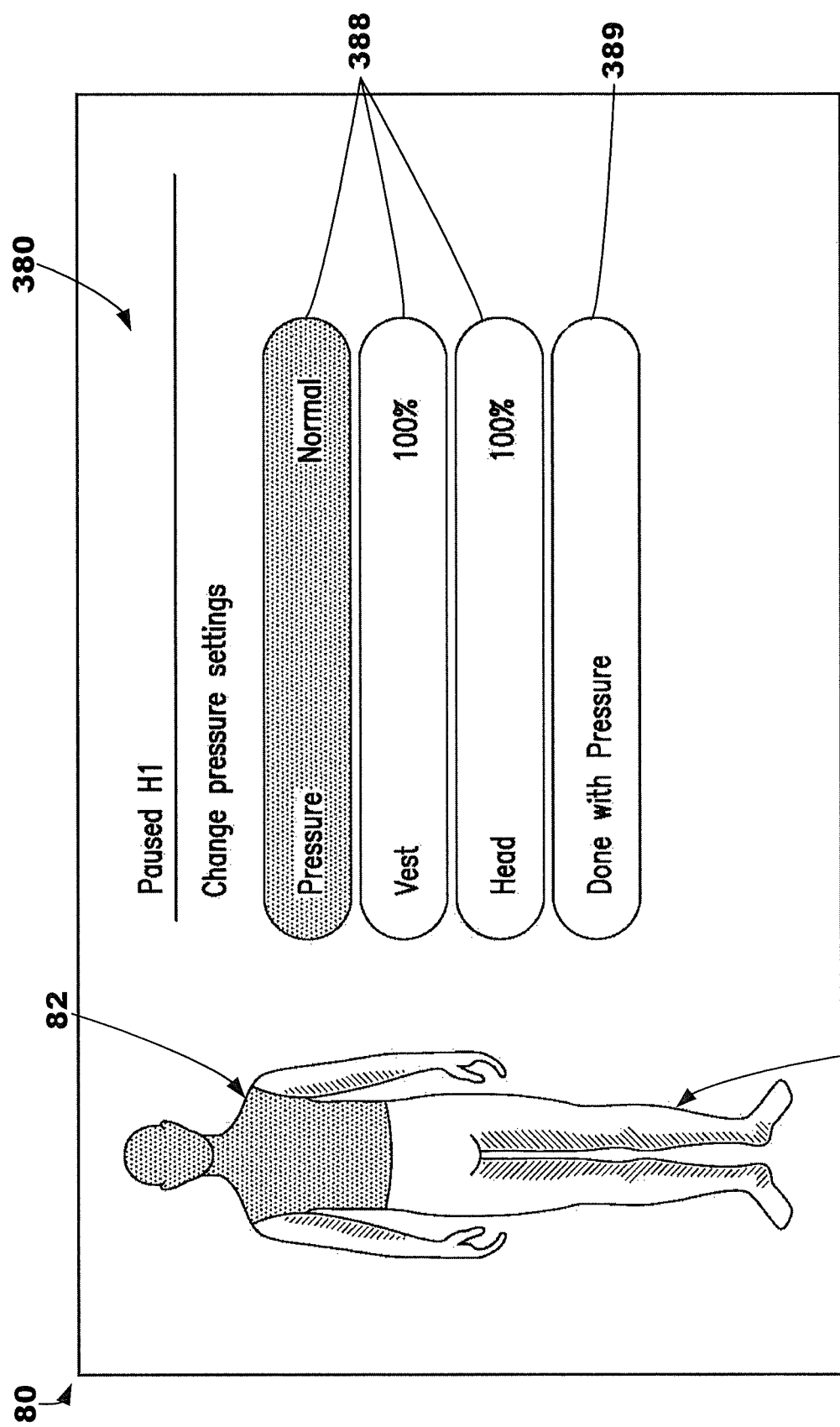

COMPRESSION GARMENT SYSTEMS

This application claims the benefit of U.S. Provisional Application No. 62/582,281, filed Nov. 6, 2017, and entitled "Compression Garment Systems," which is incorporated by reference in its entirety.

The present disclosure relates generally to compression garment systems and methods for delivering fluid to fluid cells of a compression garment and for providing a graphical user interface related to compression therapy.

Various types of compression garments are available, for example, such as for treatment of lymphedema, edema, wound healing, etc. For example, garments may include inflatable chambers or cells (or other actuatable elements) to provide compression therapy to patients and may be positioned about any body portion of a person or animal. Specifically, the garments may be positioned about body portions that exhibit swelling due to a build-up of lymph and/or other fluid and that would benefit from compression therapy provided by the garments. For example, such chambers or cells may be inflatable to one or more different pressures in a variety of sequences to provide the therapy to the patient by moving lymph from one body region to another. In other words, such compression garments may be placed around at least a portion of an individual's body for use in applying pressure to the body at one or more body regions (such as, e.g., an affected extremity). These compression garments may be donned (e.g., put on) and doffed (e.g., taken off or removed) by patients themselves or with help from others.

SUMMARY

Exemplary compression systems and methods may include one or more ways to fill the fluid cells of compression garment to provide compression therapy to one or more body portions that the compression garment is donned thereabout. While wearing the compression garment during the delivering of compression therapy, users may be positioned in a variety of positions, which may impact an amount of fluid that is used to apply a selected amount of pressure to one or more body regions of the user. For example, if a user is sitting on at least a portion of a fluid cell of a compression garment (e.g., thereby collapsing or applying pressure to one or more portions of the fluid cell), it may take less fluid being delivered to the fluid cell to provide the same amount and quality of compression therapy to a body portion than when the user is standing (e.g., such that no, or little, pressure is being applied to the fluid cell due to compression of the fluid cell by the user's body). The exemplary compression garments and methods include one or more ways that may be described as ensuring that a selected target pressure, within, e.g., a margin of error, for a fluid cell is met no matter what position the user is in or what other factors may affect the amount of fluid it may take to deliver as desired amount and quality of compression therapy.

To do so, the exemplary compression systems and methods may define a target pressure and an adjustable manifold pressure. The target pressure may be generally described as being the desired pressure for the fluid cell and the adjustable manifold pressure may be described as being a pressure value that may be modified, or adjusted, by the exemplary systems and methods and used to determine when to stop delivering fluid to the fluid cell to reach, e.g., within an appropriate or selected margin, the target pressure within the fluid cell. Additionally, the adjustment manifold pressure may be measured while fluid is being delivered to the fluid cell while the target pressure may be measured while fluid is not being delivered to the fluid cell. In other words, the adjustable manifold pressure may be measured during active fluid delivery and the target pressure may be measured during a steady state where not fluid is being delivered to the fluid cell. Further, in one or more embodiments, the exemplary compression garment apparatus may include a single pressure sensor located in a manifold configured to distribute the fluid to one fluid cell at-at-time of a plurality of fluid cells. In this way, the single pressure sensor may be used to determine the pressure within the manifold during fluid delivery so as to be compared to the adjustable manifold pressure and when fluid delivery is ceased so as to be compared to the target pressure.

The exemplary compression garment systems and methods may further include a graphical user interface that may be used by a user to provide and configure compression therapy using various compression therapy apparatus. The graphical user interface may include a human-shaped graphical element upon which a compression therapy graphical indication may be displayed, or depicted, to indicate where compression therapy on the user may be or is currently being applied. In this way, the graphical user interface may be described as providing an intuitive and unique way of providing information to users about the compression therapy, and more specifically, an intuitive and unique way of indicating where compression therapy will be or is being applied on a human body.

The exemplary compression garment systems and methods may further include processes for the identification of a compression garment using a wireless communication interface such that, for example, the compression therapy apparatus may be configured (e.g., settings selected, therapy programs customized and/or presented, etc.) based on the identification of the compression garment. For example, a user may position a leg compression garment proximate the system, and the leg compression garment may be identified via the communication interface. Thus, the system may configure compression therapy for use in with the leg compression garment and/or may select particular configuration options to be presented to a user corresponding to, or related to, the leg compression garment (e.g., may only present leg compression therapy programs to the user, etc.). Additionally, for example, a user may use a user interface device such as, e.g., a mobile phone, to communicate with the communication interface to identify the compression garment. For instance, a user may use a user interface device to select a head garment, which may be transferred to the communication interface of the system such that the system knows that a head compression garment is to be used and can configure the therapy for the head compression garment. Still further, the graphical user interface, or at least one or more graphical regions, graphical areas, or graphical elements thereof, of the compression garment system may be transmitted to and displayed on a user interface device. In this way, users may not need to have a clear line of sight of the graphical user interface of the compression garment system, and instead, may use their user interface devices to view the status of the compression garment system (e.g., therapy status) and/or to configure the configure the compression garment system.

One exemplary compression garment system may include a manifold operably couplable to at least one fluid cell of a compression garment, a pump operably coupled to the manifold to deliver fluid to the at least one fluid cell, and a controller comprising one or more processors and operably coupled to the pump. The controller may be configured to provide a target pressure for each of the at least one fluid cell, provide an adjustable manifold pressure for each of the at least one fluid cell, and deliver fluid using the pump to the at least one fluid cell until the pressure in the manifold is equal to the adjustable manifold pressure. The controller may be further configured to measure the pressure in the manifold after the pump has stopped delivering fluid to the at least one fluid cell, increase the adjustable manifold pressure and continue to deliver fluid using the pump to the at least one fluid cell until the pressure in the manifold is equal to the increased adjustable manifold pressure in response the pressure in the manifold being less than the target pressure, and decrease the adjustable manifold pressure in response the pressure in the manifold being greater than the target pressure.

One exemplary method of filling at least one fluid cell of a compression garment may include delivering fluid using the pump to at least one fluid cell until the pressure in the manifold is equal to an adjustable manifold pressure, measuring the pressure in the manifold after the pump has stopped delivering fluid to the at least one fluid cell, increasing the adjustable manifold pressure and continuing to deliver fluid using the pump to the at least one fluid cell until the pressure in the manifold is equal to the increased adjustable manifold pressure in response the pressure in the manifold being less than a target pressure, and decreasing the adjustable manifold pressure in response the pressure in the manifold being greater than the target pressure.

In one or more embodiments, the at least one fluid cell may include a plurality of fluid cells corresponding to the plurality of pressure applying regions to apply pressure to a plurality of regions of one or more body portions of a user when the compression garment is donned. Further, the target pressure may be different for at least two of the plurality of fluid cells.

In one or more embodiments, the manifold may include a plurality of ports operably couplable to a plurality of hoses to transmit fluid from the pump to the at least one fluid cell. Further, each of the plurality of ports may include a plurality of apertures, and each of the plurality of apertures may be operably coupled to a different fluid cell of the at least one fluid cell.

In one or more embodiments, the pump may be a variable rate pump, and the controller may be further configured to define a first rate of delivering of fluid to one or more fluid cells of a first type of compression garment and define a second rate of delivering of fluid to one or more fluid cells of a second type of compression garment, where the first rate is different from the second rate. Further, the first type of compression garment may be donnable about a user's head and the second type of compression garment may be donnable about one or more of a user's torso, trunk, leg, and arm. Still further, the first rate may be less than the second rate.

One exemplary compression garment system may include compression therapy apparatus operably couplable to a compression garment to provide compression therapy to a patient, a display comprising a graphical user interface to display at least information related to the compression therapy, and a controller comprising one or more processors and operably coupled to the compression therapy apparatus and the display. The controller may be configured to display a human-shaped graphical element on the graphical user interface and display a compression therapy graphical indication on the human-shaped graphical element indicative of the location of compression therapy deliverable by the compression therapy apparatus.

One exemplary method for a compression garment system may include displaying a human-shaped graphical element on a graphical user interface of a compression therapy apparatus operably couplable to a compression garment to provide compression therapy to a patient and displaying a compression therapy graphical indication on the human-shaped graphical element indicative of the location of compression therapy deliverable by the compression therapy apparatus.

In one or more embodiments, the compression therapy apparatus may include a pump operably couplable to at least one fluid cell of a compression garment to deliver compression therapy to the patient.

In one or more embodiments, the human-shaped graphical element may depict a plurality of body regions and the compression therapy graphical indication is displayed on at least one body region of the plurality of body regions to indicate that compression therapy is deliverable thereto.

In one or more embodiments, the controller may be further configured to execute or the method may further include providing a therapy configuration graphical region on the graphical user interface to allow a user to configure the compression therapy to be delivered to the patient, and the human-shaped graphical element may be displayed on the graphical user interface with the therapy configuration graphical region and the compression therapy graphical may indicate the location of compression therapy configured using the therapy configuration graphical region. Further, the therapy configuration graphical region may include a plurality of selectable treatment regions selectable by a user to select which one or more body regions of the patient to deliver compression therapy to. Still further, upon selection of a treatment region of the plurality of treatment regions, the therapy configuration graphical region may include a plurality of selectable treatment areas selectable by a user to select one or more body areas of the patient to deliver compression therapy to, where the one or body areas are a subset of the selected one or more body portions. Sill further, each of the plurality of selectable body areas may include a treatment duration indicating an amount of time that compression therapy is be delivered to the corresponding body area of the patient. Still further, two or more of the plurality of selectable treatment regions may be selectable by a user to select two or more body regions of the patient to deliver compression therapy to during a single treatment. Still further, the therapy configuration graphical region may include a plurality of treatment pressure variation regions selectable by a user to increase, decrease, or maintain the pressure of the compression therapy. Still further, the therapy configuration graphical region may include a plurality of treatment cycle regions selectable by a user to select an amount of cycles of the compression therapy.

In one or more embodiments, the controller may be further configured to execute or the method may further include providing a therapy status graphical region on the graphical user interface to allow a user to view status information regarding the compression therapy being delivering to the patient, and the human-shaped graphical element may be displayed on the graphical user interface with the therapy status graphical region. Further, the therapy status graphical region may include a therapy duration area depicting an amount of time remaining for one or more cycles of the compression therapy and a pause/resume area to allow a user to pause or resume the compression therapy being delivered.

In one or more embodiments, the controller may be further configured to execute or the method may further include delivering compression therapy to at least the head and another body portion of the patient.

In one or more embodiments, the controller may be further configured to execute or the method may further include allowing a user to save a therapy configuration and displaying a preset region selectable by the user to configure compression therapy according to the saved therapy configuration. Further, in one or more embodiments, the controller may be further configured to execute or the method may further include defining a default therapy configuration and displaying a default therapy region selectable by the user to configure compression therapy according to the default therapy configuration.

One exemplary compression garment system may include compression therapy apparatus operably couplable to a compression garment to provide compression therapy to a patient, a display comprising a graphical user interface to display information related to the compression therapy, a communication interface comprising an antenna, and a controller comprising one or more processors and operably coupled to the compression therapy apparatus and the communication interface. The controller may be configured to identify the compression garment using the communication interface and configure compression therapy to be delivered by the compression garment based on the identity of the compression garment.

One exemplary method for use with compression therapy apparatus including a compression garment may include identifying a compression garment using a communication interface comprising an antenna and configuring compression therapy to be delivered by the compression garment based on the identity of the compression garment.

In one or more embodiments, identifying the compression garment using the communication interface may include identifying the compression garment using radiofrequency identification (RFID). Further, in one or more embodiments, identifying the compression garment using the communication interface may include identifying the compression garment using Bluetooth. Still further, in one or more embodiments, identifying the compression garment using the communication interface may include receiving the identity of the compression garment from a user interface device.

In one or more embodiments, the controller may be further configured to execute or the method may further include allowing user to configure the compression therapy using a user interface device and receiving the compression therapy configuration using the communication interface from the user interface device.

In one or more embodiments, the controller may be further configured to execute or the method may further include transmitting a therapy status information to a user interface device so that the therapy status information is displayable on a graphical user interface of the user interface device. The therapy status graphical information may include a therapy duration area depicting an amount of time remaining for one or more cycles of the compression therapy and a pause/resume area to allow a user to pause or resume the compression therapy being delivered.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIGS. 11A-11F is an exemplary graphical user interface of the exemplary system and controller of FIGS. 1-3 and 5 depicting a therapy configuration graphical region being used to setup a compression therapy.

FIGS. 12A-12C are exemplary graphical user interfaces of the exemplary system and controller of FIGS. 1-3 and 5 depicting compression therapy adjustment.

DETAILED DESCRIPTION OF EXEMPLARY EMBODIMENTS

Figure 1:
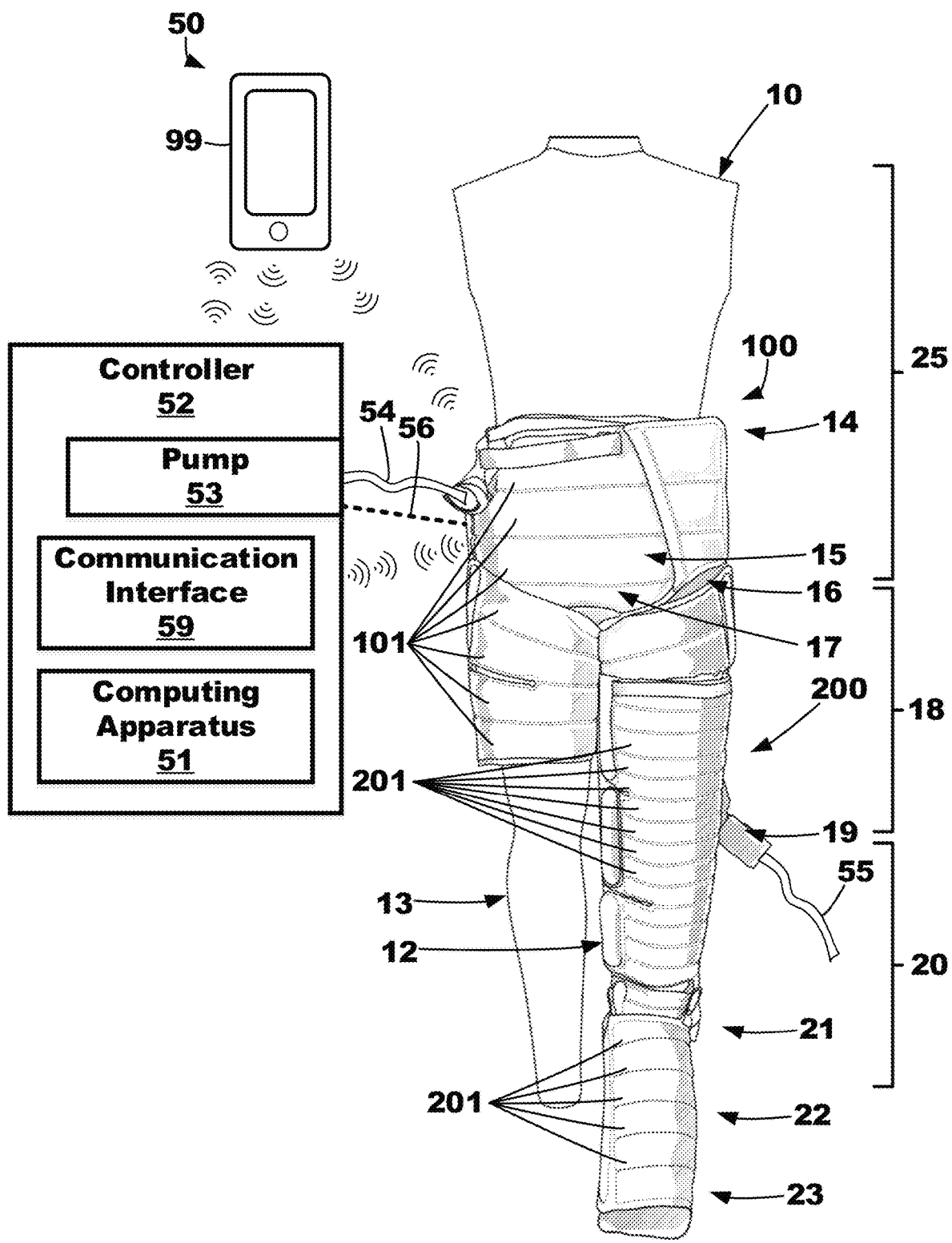
FIG. 1 is a front perspective of an exemplary compression system including a trunk garment and a leg garment located on a body.

In the following detailed description of illustrative embodiments, reference is made to the accompanying figures of the drawing, which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary apparatus, systems, structures, and methods shall be described with reference to FIGS. 1-12. It will be apparent to one skilled in the art that elements from one embodiment may be used in combination with elements of the other embodiments, and that the possible embodiments of such apparatus, systems, structures, and methods using combinations of features set forth herein is not limited to the specific embodiments shown in the Figures and/or described herein. Further, it will be recognized that the embodiments described herein may include many elements that are not necessarily shown to scale. Still further, it will be recognized that the size and shape of various elements herein may be modified but still fall within the scope of the present disclosure, although certain one or more shapes and/or sizes, or types of elements, may be advantageous over others.

The present disclosure relates generally to compression garments that include garment portions that are configured to be donned on at least a portion of a body (e.g., person, animal, etc.) and configured to apply pressure to that portion of the body, compression garment systems that include compression garments and apparatus for controlling pressure applied to at least a portion of a body, and methods using such compression garments and compression garment systems (e.g., methods of controlling pressure applied to the body, methods of providing and displaying graphical user interfaces, methods of configuring compression therapy, methods of identifying compression garments, etc.)

Compression garment systems (e.g., such as compression garments described in U.S. Pat. No. 6,179,796 entitled "Lymphedema treatment system," U.S. Pat. No. 6,645,165 entitled "Lymphedema treatment system," U.S. Pat. No. 6,860,862 entitled "Lymphedema Treatment System," and U.S. Pat. No. 6,966,884 entitled "Lymphedema Treatment System," which are herein incorporated by reference and which may modify and be modified with features described herein) may be used for various reasons including therapy for people with lymphedema, animals requiring therapy, wound therapy, etc. As used herein, the term body refers to not only humans but any other animal species that may benefit from the concepts and features described herein. These compression garments may be placed around at least a portion of an individual's body and used to apply pressure to the body at an affected extremity (e.g., leg, head, neck, arm, torso, a shoulder, etc.). Some embodiments described herein may include a compression system having a garment configured to be positioned on (e.g., wrapped around, placed adjacent, located in proximity to, etc.) at least a portion of a body (e.g., trunk, leg, foot, arm, torso, shoulder, head, neck, etc.). The compression garments may be donned (e.g., put on) and doffed (e.g., taken off) by individuals themselves or with help from others. The garment may also include one or more chambers (e.g., cells, compartments, sealed volumes, bladders etc.) distributed (e.g., distributed throughout, distributed in concentric patterns "radiating" away from a central point or axis, along a length, etc.) of the garment configured to receive a fluid (e.g., air) to perform compression therapy.

The compression therapy provided by the compression garment systems may help to treat lymphedema. Lymphedema is a condition of localized fluid retention and tissue swelling that may be inherited, caused by cancer treatments, caused by parasitic infections, injury, etc. For example, lymphedema of the legs may cause swelling around the feet, ankles, calves, knees, thighs, etc. Compression garments described herein covering the leg and trunk may be used by an affected individual to provide a therapeutic benefit. Specifically, the compression garments may be configured to manipulate lymph nodes or vessels by applying pressure to move lymph toward more beneficial locations (e.g., toward drainage areas, away from affected regions, etc.). For example, compression therapy using the systems described herein may be performed around the leg and trunk regions to help treat lymphedema in the leg and trunk regions by, e.g., moving lymph upward towards the upper torso, moving lymph downward away from the upper torso, etc.

The compression garments described herein may be configured to apply pressure to the affected regions of the body to apply compression therapy. The compression garments may include various portions that each includes controllable pressure applying regions. Each controllable pressure applying region may be configured to apply pressure to a specific portion of the body (e.g., at a specific time during therapy). The controllable pressure applying regions may work in combination with one another to help provide therapy by applying a sequence of pressures on the body that moves lymph in a desired direction (e.g., from the feet towards the trunk, from the trunk towards the feet, from the feet towards the calf, from the ankle towards the thigh, etc.). Such application of a sequence of pressures on the body that moves lymph (e.g., pressure being applied to one or more portions of the legs, feet, and trunk, at different times during a compression therapy period) may be referred to as applying dynamic pressure to the body. The sequence of pressures may be referred to as pressure gradients, e.g., from a distal region (e.g., feet, toes, ankle, etc.) to a proximal region (e.g., trunk, torso, etc.). Additionally, in some embodiments, dynamic pressure may not be applied sequentially, and instead, be applied non-sequentially as will be further described herein.

The controllable pressure applying regions of the compression garments may also apply static pressure to the body. For example, the compression garments may apply a constant pressure when a portion of the garment is positioned on the body over a therapy time period (e.g., static pressure over the therapy time period) or may apply a pressure that may be controlled to change over time during the therapy time period (e.g., dynamic pressure). In one or more embodiments, the dynamic pressure may be applied to the portion of the body through one or more chambers in the compression garment. The one or more chambers may be configured to receive fluid. Alternately, or in combination with one or more fluid receiving chambers, such pressures may be applied using one or more actuatable elements in the compression garment configured to apply pressure to the body (e.g., electrically controlled materials suitable to provide compression).

An exemplary compression garment system 50 including a trunk compression garment 100 configured to be positioned around at least a portion of a trunk 25 and legs 12, 13 of a human body 10 and a leg compression garment 200 configured to be positioned around at least a portion of the left leg 12 of the human body 10 is shown in FIG. 1. The trunk garment 100 and the leg garment 200 may be used in conjunction or apart from each other to provide compression therapy to the body 10. Although, in the embodiment depicted, the trunk garment 100 and one leg garment 200 are donned by the body 10, it to be understood that what is depicted in FIG. 1 is only one configuration and the trunk and leg garments 100, 200 may be used in many other configurations. For example, two leg garments 200 may be used at the same time with or without the trunk garment 100. Further, for example, the trunk garment 100 may be used by itself. Still further, for example, one leg garment 200 may be used about the right leg 12 with or without the trunk garment 100.

Additionally, although trunk and leg garments 100, 200 are depicted in FIG. 1, it is to be understood that the exemplary systems, apparatus, and methods described herein may be used with any number of different compression garments such as, e.g., arm compression garments, chest compression garments, chest and arm compression garments, neck compression garments, head compression garments, etc.

The trunk garment 100 and the leg garment 200 may each define, or include, a plurality of pressure applying regions that are controllable or configurable to apply pressure to portions of the body 10. For example, the trunk garment 100 may include trunk pressure applying regions 101 that are controllable or configurable to apply pressure to one or more portions or regions of the torso, or trunk, 25 such as, e.g., to the abdominal region 14, the pelvic region 15, the coxal region 16, the groin region 17, and the femoral region 18. For example, the leg garment 200 may include leg pressure applying regions 201 that are controllable or configurable to apply pressure to one or more portions or regions of the legs 12, 13 such as, e.g., to the femoral region 18, the patellar region 19, the crural region 20, the tarsal region 21, the pedal, or foot, region 22, and the digital/phalangeal region 23. In one or more embodiments, the trunk and leg garments 100, 200 may include an exterior material covering the pressure applying regions.

The one or more pressure applying regions 101, 201 may include fluid chambers or cells, pneumatic pressure applying regions, actuatable elements, hydraulic pressure applying regions, etc. In one or more embodiments, the one or more pressure applying regions 101, 201 may include one or more chambers configured to receive fluid, and the system 50 may further include a controller 52 configured to apply pressure to one or more portions or regions of the body 10 using the one or more chambers through the control of fluid provided thereto, e.g., fluid flow, air flow, etc. For example, the trunk garment 100 may include one or more trunk garment ports through which fluid may be provided to the one or more chambers via tubing 54, and the leg garment portion 200 may include one or more leg garment ports through which fluid may be provided to the one or more chambers via tubing 55.

Further, in one or more embodiments, the pressure applying regions 101, 201 may include one or more actuatable elements (e.g., non-fluid receiving regions) configured to apply pressure to the one or more body portions or regions (e.g., an electrical signal may be used to actuate an element within the garment, such as electrically actuatable fibers in the garment, such that the compartment including such fibers applies a pressure to a portion or region of the body). In one or more embodiments, the one or more pressure applying regions 101, 201 may include both one or more chambers configured to receive fluid and one or more actuatable elements.

Any number of pressure applying regions 101, 201, some of which are labeled in FIG. 1, may be configured in the trunk and leg garment 100, 200, respectively, such that the pressure applying regions 101, 201 may be controlled to move lymph as described herein. For example, as shown in FIG. 1, the trunk garment 100 includes eight pressure applying regions 101 and the leg garment 200 includes twenty-two pressure applying regions 201. However, such pressure applying regions 101, 201 may include any number of different and separate chambers along the wrappable length of the garments 100, 200 and controllable to produce desired lymph movement (e.g., multiple chambers along the length of the trunk and leg garments 100, 200 to move lymph generally vertically in a downward or upward direction, etc.).

The controller, or control apparatus, 52 may be configured to, among other things, control the pressure applied to one or more portions or regions of the body 10 using each of the pressure applying regions 101, 201 of the garments 100, 200. For example, the controller 52 may control the pressure applied to the one or more portions or regions of the body 10 by using each of the pressure applying regions 101, 201 independent from one another or at the same time. Further, for example, the pressure applying regions 101, 201 may be controlled in groups or combinations. In one or more embodiments, the controller 52 may be configured to control the pressure applying regions 101, 201 in a variety of different sequences (e.g., applying pressure in a predetermined manner) that may be, e.g., suitable for carrying out, or performing, lymphedema therapy.

Although the controller 52 is described herein with respect to the trunk and leg garments 100, 200, it is to be understood that the controller 52 may be used (e.g., control compression therapy using, provide fluid to fluid cells of, etc.) a variety of different compressions garments such as, e.g., head compression garments, arm compression garments, chest and arm compression garments, chest compression garments, neck compression garments, etc. Additionally, it is to be understood that the controller 52 may be configured to provide compression therapy using more than one compression garment simultaneously or at-a-time. For example, as shown with respect to FIG. 1, the controller 52 may control and/or provide compression therapy using both the trunk compression garment 100 and a leg compression garment 200. Further, for example, the controller 52 may control and/or provide compression therapy using both a chest compression garment and a head compression garment. Still further, for example, the controller 52 may control and/or provide compression therapy using both a chest and arm compression garment and a trunk compression garment. And still further, for example, the controller 52 may control and/or provide compression therapy using both a left leg compression garment and a right leg compression (e.g., using an adapter to expand the number of ports from four to eight). Yet still further, for example, the controller 52 may control and/or provide compression therapy using a left leg compression garment, a right leg compression, and a trunk garment.

Further, the controller 52 may control the pressure based on one or more pressures measured by one or more pressure sensors associated with, or part of, the controller 52 and/or the garments 100, 200. For example, pressure sensors may be implemented for sensing pressure in a plurality of different manners at, e.g., a manifold for multiple chambers, each pressure applying region, each air cell or chamber, etc. For instance, one or more pressure sensors may be located in a manifold that distributes fluid to one or more fluids cells of the pressure applying regions of various compression garments such as the pressure applying regions 101, 201. Further, for instance, one or more pressure sensors may be provided in the garments 100, 200 proximate the pressure applying regions 101, 201. Still further, pressure sensing apparatus may take the form of using pressure sensors within the garment as described in U.S. Pat. No. 9,027,408 entitled "Elastomeric Particle Having An Electrically Conducting Surface, A Pressure Sensor Comprising Said Particles, A Method For Producing Said Sensor And A Sensor System Comprising Said Sensors," or a pump or control apparatus may be provided with pressure sensing functionality (e.g., measuring pressures of air in chambers as part of the pump apparatus) such as described in U.S. Pat. No. 7,947,003 entitled "Pressurized Medical Device," all of which are incorporated by reference herein. One or more compression garments that may be modified with features (e.g., sensors) described herein may be similar to and include one or more features found in U.S. Pat. No. 6,860,862 entitled "Lymphedema Treatment System," U.S. Pat. No. 6,966,884 entitled "Lymphedema Treatment System," U.S. Pat. No. 6,179,796 entitled "Lymphedema treatment system," and U.S. Pat. No. 6,645,165 entitled "Lymphedema treatment system," which are herein incorporated by reference.

The controller 52 may further include computing apparatus 51, which may include one or more processors employing one or more programs or routines carrying out one or more methods or processes and implemented with one or more types of memory, may be described as being configured to control the system and/or one or more elements thereof (e.g., adjusting the delivery of fluid to one or more fluids cells of a compression garment, displaying a graphical user interface used to configure compression therapy and/or view the status of ongoing compression therapy, identifying a compression garment using a communication interface that may be wireless, providing compression therapy using the one or more pressure applying regions, etc.). In one or more embodiments, the computing apparatus 51 may be configured to control the compression system using wired and/or wireless technology.

The methods and/or logic and/or configurations described in this disclosure, including those attributed to the systems, or various constituent components, may be implemented, at least in part, in hardware, software, firmware, or any combination thereof. For example, various aspects of the techniques may be implemented within one or more processors, including one or more microprocessors, microcontrollers, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices (e.g., within the system, outside of the system, or a combination of both) to support the various operations and functions described in this disclosure. In addition, any of the described components may be implemented together or separately as discrete but interoperable logic devices. Description of different features is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

Further, the controller 52 may include a pump 53 that may be controlled by the computing apparatus 51 to provide a fluid (e.g., air) to/from the plurality of pressure applying regions 101, 201, which may be a plurality of fluid cells or chambers. For example, the pump 53 may be connected to the plurality of fluid cells, or chambers, corresponding to the plurality of pressure applying regions 101, 201 by tubing 54, 55 so as to provide flow of fluid thereto or removal of fluid therefrom.

Figure 2:
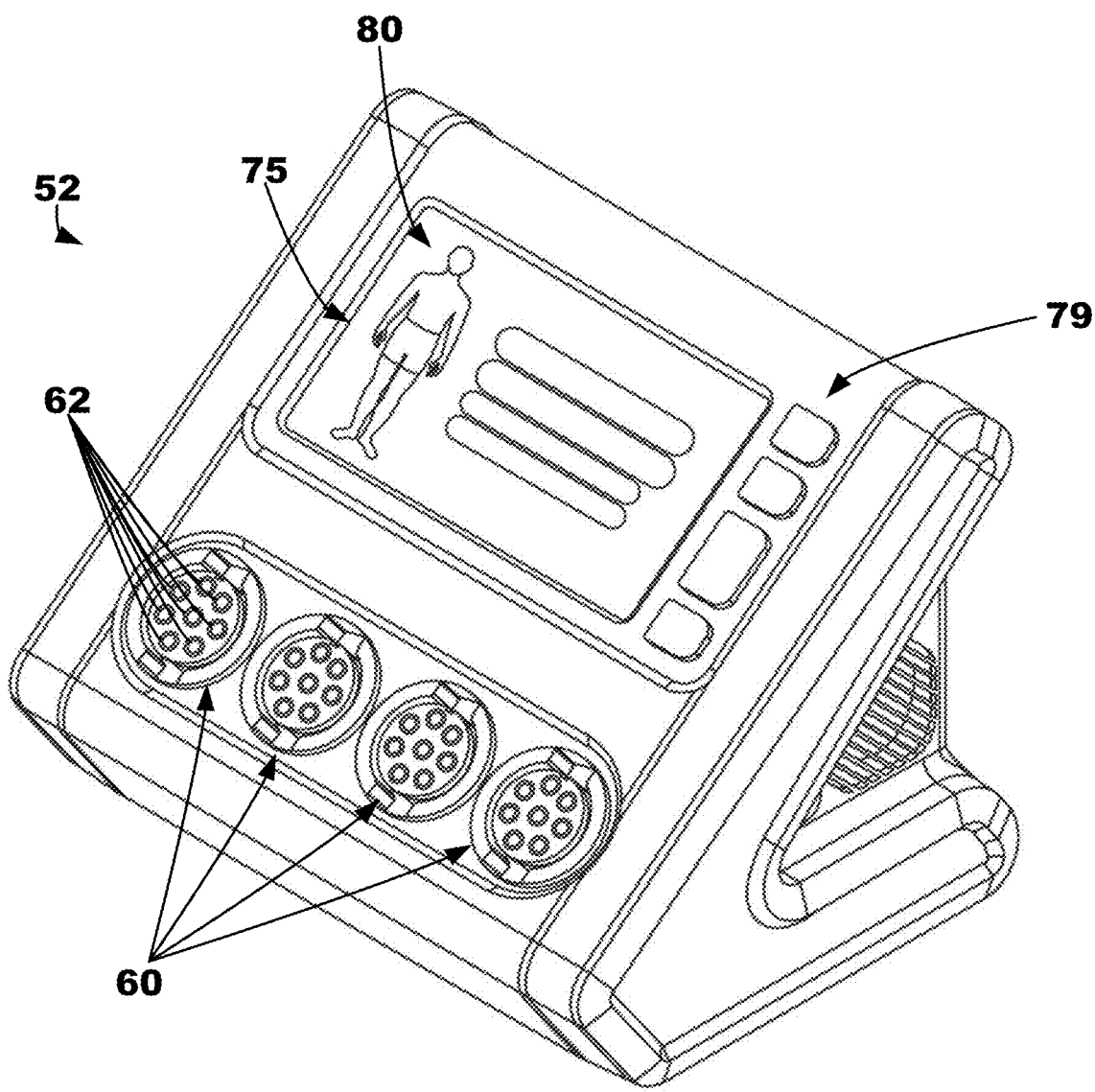
FIG. 2 is a perspective view of an exemplary compression garment controller.

One exemplary embodiment of a controller 52 is depicted in FIG. 2. As shown, the controller 52 may include a plurality of ports 60. As depicted, the controller 52 includes, or defines, four ports 60. However, it is to be understood that some embodiments may include more than four ports 60 and some embodiments may include less than four ports 60. Each of the ports 60 may be operably couplable to a hose (or tubing), such as hoses 54, 55, that are, in turn, operably coupled a compression garment. Each of the hoses 54, 55 may include multiple fluid lines, and each of the fluid lines may be operably coupled to a different fluid cell of the compression garment that the hoses are operably coupled thereto.

Each of the ports 60 of the controller 52 may include a plurality of apertures 62, and each of the apertures 62 may be operably couplable to a fluid line of a hose operably coupled to the respective port 60. Thus, each of the apertures 62 may be operably coupled to a different fluid cell of a compression garment when the hose of the compression garment is operably coupled to a port 60 of the controller 52.

The controller 52 may further include a display 75 displaying, or depicting, a graphical user interface 80, which will be described further herein with respect to the FIGS. 5-11, and input apparatus 79 (e.g., a plurality of buttons) configured to allow users to interact with the controller 52 to, e.g., configure therapy, "power on" the controller 52, etc. More specifically, the computing apparatus 51 of the controller 52 may be configured to receive input from input apparatus 79 and transmit output to the display 75. Further, although not depicted, the computing apparatus 51 may include data storage that may allow for access to processing programs or routines and one or more other types of data (e.g., target pressures, adjustable manifold pressures, compression garment identification information, graphical regions, graphical elements, graphical areas, saved compression therapy programs, default compression therapy programs, increased pressure values, decreased pressure values, baseline pressure values for fluid cells, baselines pressure values per compression garment, metrics, variables, images, values, limits, text strings, macros, etc.) that may be employed to perform, or carry out, exemplary methods and/or processes (e.g., performing fluid cell filling routines, measuring pressures, delivering fluid to fluid cells, configuring compression therapy, saving compression therapy programs, identifying compression garments using a communication interface, displaying graphical user interfaces, allowing user interaction with graphical user interfaces, displaying graphical elements, displaying textual elements, displaying textual values, notifying operators/users of problems, etc.) for use in performing or configuring compression therapy. The computing apparatus 51 may be operatively coupled to the input apparatus 79 and the display 75 to, e.g., transmit data to and from each of the input apparatus 79 and the display 75. For example, the computing apparatus 51 may be operatively coupled to each of the input apparatus 79 and the display 75 using, e.g., analog electrical connections, digital electrical connections, wireless connections, bus-based connections, etc. As described further herein, an operator, or user, may provide input to the input apparatus 79 to manipulate, or modify, one or more graphical elements, graphical regions, and graphical areas displayed on the display 75 to, e.g., initiate one or more actions and/or processes related to the compression therapy system, indicate one or more actions and/or statuses related to one or more processes of the compression therapy system, etc.

The input apparatus 79 may include any apparatus capable of providing input to the computing apparatus 51 to perform the functionality, methods, and/or logic described herein. In this embodiment, the input apparatus 79 includes a plurality of user-actuatable buttons such that a user may interact with the graphical user interface 80 displayed on the display 75. In at least one embodiment, the buttons may control an indication or cursor that may be used to select a graphical region, graphical area, graphical element, etc. of the graphical user interface 80. In at least one embodiment, each of the buttons may correspond to "soft" buttons that are displayed on the graphical user interface 80 such that, e.g., selection of a button will initiate the action of the corresponding "soft" button displayed on the graphical user interface 80.

In other embodiments, the input apparatus 79 may include a touchscreen (e.g., capacitive touchscreen, a resistive touchscreen, a multi-touch touchscreen, etc.), a mouse, a keyboard, a trackball, etc. A touchscreen may be part of (e.g., overlay) the display 75 such that, e.g., a user may use the touchscreen to interact (e.g., by touch) with a graphical user interface 80 displayed on the display 75. For example, the input apparatus 79 may allow a user to interact with a graphical user interface containing, or depicting, graphical elements, graphical regions, and graphical areas associated with and representative of (or corresponding to) one or more features or processes of the compression therapy system.

The display 75 may include any apparatus capable of displaying information to a user, such as a graphical user interface, etc., to perform the functionality, methods, and/or logic described herein. For example, the display 75 may include a liquid crystal display, an organic light-emitting diode screen, a touchscreen, a cathode ray tube display, etc. As described further herein, the display 75 may be configured to display a graphical user interface 80 that includes one or more graphical regions, graphical areas, and graphical elements.

As used herein, a "region" of a graphical user interface may be defined as a portion of the graphical user interface within which information may be displayed or functionality may be performed and/or controlled by a user. Regions may exist within other regions, which may be displayed separately or simultaneously. For example, smaller regions may be located within larger regions, regions may be located side-by-side, etc. Additionally, as used herein, an "area" of a graphical user interface may be defined as a portion of the graphical user interface located within a region that is smaller than the region within which the area is located. Still further, as used herein, an "element" of a graphical user interface may be defined as a component of the graphical user interface that may be located within, or adjacent to, a region, an area, or another element. In one or more embodiments, an "element" of a graphical user interface may include a perimeter, or border, defining the outer edge, or boundary, of the element. In one or more embodiments, an "element" of a graphical user interface is a defined, finite portion, item, and/or section of a graphical user interface.

Additionally, as shown in FIG. 1, in one or more embodiments, the controller 52 may be connected to one or more components of the compression garment system 50 via one or more electrical lines as represented generally by dashed line 56 and/or wirelessly as represented generally by the wireless signal lines in FIG. 1. For example, the controller 52 may be connected to communicate with and to control the pressure applying regions (such as, e.g., fluid cells and/or electrically actuatable pressure applying regions of the garment configured to apply pressure to the body) either with use of physical electrical connections and/or wirelessly. Further, for example, the controller 52 may further include a communication interface 59 to, e.g., communicate with a compression garment 100, 200, communicate with a user interface device 99, etc. as represented generally by the wireless signal lines in FIG. 1. The communication interface 59 may be wireless interface that includes an antenna for sending and receiving signals using various wireless protocols such as, e.g., BLUETOOTH, WIFI, radiofrequency identification (RFID), etc.

In one or more embodiments, the controller 52 may be configured to identify a compression garment using the communication interface 59. For example, data about, or regarding, the compression garment may be transmitted to the controller 52 via the communication interface 52. Such data may include various information about the compression garment such as, for example, a serial number or unique identifier, a model number, a number of fluid cells that garment has, the size of the compression garment, the date of manufacturer, an expiration date, etc.

In response to receiving the data regarding the compression garment via the communication interface 59, the computing apparatus 51 of the controller 52 may configure compression therapy to be delivered by the compression garment based at least on the identity of the compression garment. For instance, different compression garments may utilize different compression therapy settings such as, e.g., different pressures, different durations, different pump, or fluid delivery, rates, etc., and the computing apparatus 51 may tailor, or customize, the compression for the identified compression garment.

Further, in one or more embodiments, the computing apparatus 51 may customize what is displayed to the user on the graphical user interface 80 based upon the identification of the compression garment. For example, if a leg garment is identified by the controller 52 via the communication interface 59, then the computing apparatus 51 may only, or may first, display leg compression therapy settings to a user. In this way, a user may not need to input, or select, the compression garment being used into the controller 52 prior to or during configuration of compression therapy using the controller 52.

The data regarding the compression garment may be transferred to the controller 52 via the communication interface from the compression garment itself or another device. For example, the compression garment may include a wireless tag that when interrogated by the communication interface 59 will send data regarding the compression garment such as, e.g., identification information, to the communication interface 59. Further, for example, a user interface device 99 such as, e.g., a mobile telephone or other computing device, may wirelessly transmit data regarding the compression garment to the communication interface 59. In this way, a user may use an application, or app, running on their mobile telephone to instruct the controller 52 which compression garment the user will be using for compression therapy in conjunction with the controller 52. Further, the graphical regions, graphical areas, and/or graphical elements of the exemplary graphical user interfaces described herein may be transmitted via the communication interface 59 to a user interface device 99 such that, for example, a user may use their user interface device 99 to configure and/or interact with the controller 52 to, e.g., deliver and configure compression therapy in the same or similar way as shown in the various graphical regions, graphical areas, and graphical elements of the graphical user interface 80 of the controller 52 depicted herein. In other words, the graphical regions, graphical areas, and graphical elements of the graphical user interface 80 of the controller 52 depicted herein may be wirelessly transmitted to a user's user interface device 99 (e.g., such as a mobile phone) such that a user may interact with their user interface device 99 to configure compression therapy, initiate compression therapy, stop or pause compression therapy, etc.

The pressure applying regions 101, 201 of the garments 100, 200 may be described as being controllable since the pressure applying regions 101, 201 are under control of controller 52. Thus, the system 50, using the controller 52, may be configured to provide compression therapy to an individual (e.g., a patient) wearing the garments 100, 200 such that lymph flows throughout the body 10 in desired directions, e.g., such as from the leg or legs 12, 13 to the trunk, or torso, 25 of the body 10, from the trunk, or torso, 25 to the leg or legs 12, 13 of the body 10, etc. In other words, by controlling the pressure applying regions 101, 201 in a variety of different sequences (e.g., applying pressure in a predetermined manner), for example, lymph may flow generally from the legs 12, 13 and lower trunk of the body 10 towards the upper trunk of the body 10. The direction of lymph flow from the legs 12, 13 to the trunk 25 of the body 10 may provide relief to an individual by moving excess lymph from the legs 12, 13, and ultimately, moving such lymph towards and into one or more regions of the trunk 25 such as, e.g., the right axillary nodes located proximate a right under arm region and the left axillary nodes located proximate a left under arm region.

The pressure applying regions 101, 201 of the trunk and leg garments 100, 200 can be described as either providing a normal, or first, pressure value or providing an increased, or second, pressure value (e.g., the increased, or second, pressure value being greater than the normal, or first, pressure value). In at least one embodiment, the first, or normal, pressure value for the pressure applying regions 101, 201 of the trunk and leg garments 100, 200 is about 0 mmHG, about 10 mmHG, about 20 mmHG, about 30 mmHG, about 50 mmHg, about 60 mmHG, etc. (over atmospheric pressure) and the second, or increased, pressure value for the pressure applying regions 101, 201 of the trunk and leg garments 100, 200 is about 30 mmHG, about 40 mmHG, about 45 mmHG, about 50 mmHG, about 70 mmHg, about 100 mmHG, etc. (over atmospheric pressure). For example, the first, or normal, pressure value for the pressure applying regions 101, 201 of the trunk and leg garments 100, 200 may be greater than or equal to about 0 mmHg, greater than or equal to about 5 mmHg, about 10 mmHg, greater than or equal to about 20 mmHg, greater than or equal to about 30 mmHg, greater than or equal to about 40 mmHg, greater than or equal to about 50 mmHg, greater than or equal to about 60 mmHg, etc. Further, for example, the first, or normal, pressure value for the pressure applying regions 101, 201 of the trunk and leg garments 100, 200 may be less than or equal to about 80 mmHg, less than or equal to about 70 mmHg, less than or equal to about 55 mmHg, less than or equal to about 45 mmHg, less than or equal to about 35 mmHg, etc. For example, the second, or increased, pressure value for the pressure applying regions 101, 201 of the trunk and leg garments 100, 200 may be greater than or equal to about 20 mmHg, greater than or equal to about 40 mmHg, greater than or equal to about 50 mmHg, greater than or equal to about 60 mmHg, greater than or equal to about 70 mmHg, greater than or equal to about 80 mmHg, greater than or equal to about 90 mmHg, greater than or equal to about 105 mmHg, greater than or equal to about 120 mmHg, greater than or equal to about 140 mmHg, greater than or equal to about 160 mmHg, greater than or equal to about 190 mmHg, etc. For example, the second, or increased, pressure value for the pressure applying regions 101, 201 of the trunk and leg garments 100, 200 may be less than or equal to about 300 mmHg, less than or equal to about 250 mmHg, less than or equal to about 200 mmHg, less than or equal to about 175 mmHg, less than or equal to about 150 mmHg, less than or equal to about 130 mmHg, less than or equal to about 110 mmHg, less than or equal to about 100 mmHg, less than or equal to about 95 mmHg, less than or equal to about 85 mmHg, less than or equal to about 75 mmHg, less than or equal to about 65 mmHg, less than or equal to about 45 mmHg, less than or equal to about 30 mmHg, etc.

Figure 3:
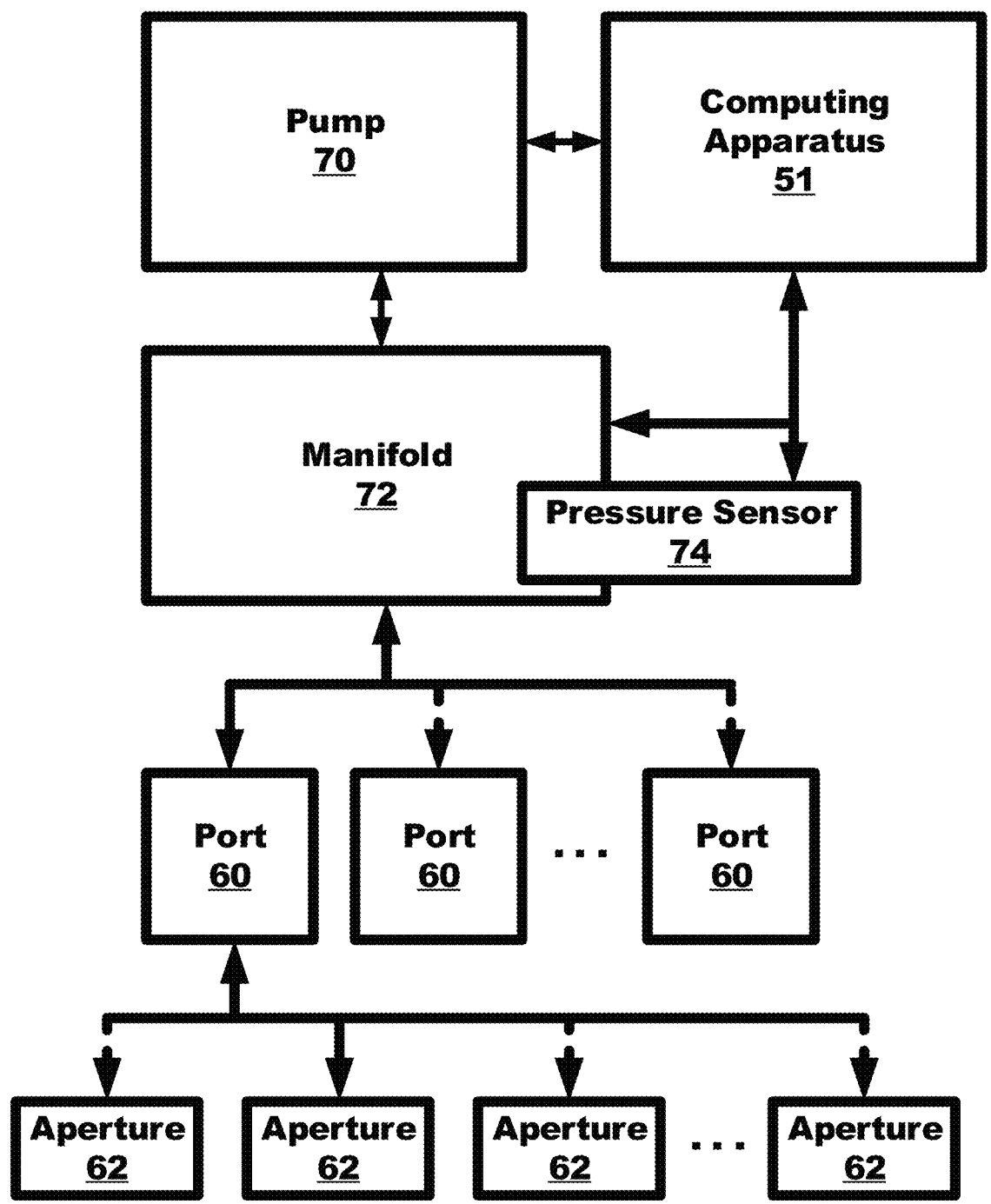
FIG. 3 is diagram of an exemplary compression garment controller.

One embodiment of an exemplary compression garment controller 52 is diagrammatically depicted in FIG. 3. As shown, the controller 52 may include a pump 70 that is operatively coupled to the computing apparatus 51 such that, for example, the computing apparatus 51 may control operation of the pump 70 to deliver fluid to one or more fluid cells of a compression garment.

The controller 52 may further include a manifold 72 that is operatively coupled to the pump 70 to receive fluid (e.g., air) therefrom and to the computing apparatus 51 to receive control information (e.g., such that the computing apparatus 51 may control the manifold). Generally, the manifold 72 may be configurable or operable to select what fluid cells of one or more compression garments connected thereto will receive fluid. To do so, the manifold 72 may include a plurality of valves that are controlled by the computing apparatus 51. The plurality of valves may select which of the plurality of ports 60 are to be operatively coupled to the pump 70 receive fluid therefrom and further which of the plurality of apertures 62 of the selected ports 60 are to be operatively coupled to the pump 70 receive fluid therefrom. In other words, using a plurality of valves of the manifold 72, one or more of the ports 60 may selected, and then one or more apertures 62 of those selected ports 62 may be selected to receive fluid from the pump 70. In this way, the computing apparatus 51 may control which of the fluid cells of the compression garment that are operably coupled to the controller 52 via the ports 60 and apertures 62. As shown in FIG. 3, a single aperture 62 of one of the ports 60 is selected using valves of the manifold 72 as indicated by the solid line extending thereto while the other ports 60 and apertures 62 have dotted lines extending thereto (e.g., indicating that valves of the manifold 72 have closed those fluid paths). Further, although only one of the ports 60 is shown to include a plurality of apertures 62, it is to be understood that each of the ports 60 may include a plurality of apertures, e.g., as shown in FIG. 2. Further, although not shown, it is to be understood that the manifold may be selectively vented (e.g., via one or more valves) to, e.g., release fluid from one or more fluid cells that are operatively coupled to the manifold 72. In this way, the manifold 72 may be used to operatively fill or empty each of the plurality of fluid cells via the ports 60 and apertures 62 thereof.

The controller 52 may further include a pressure sensor 74 located in the manifold 72 to measure pressure therein. When a single aperture 62 of a port 60 is selected such that the manifold 72 is operably coupled to the single aperture 62, and thus, also operably coupled to a single fluid cell of a compression garment coupled thereto, the pressure sensor 74 may effectively measure the pressure of the fluid cell. Additionally, the pressure sensor 74 may be configured to measure a pressure value while the pump 70 is running or while the pump 70 is stopped. In this way, a pressure value may be measured from the manifold 72 during delivery of fluid from the pump 70 to a fluid cell, and such value may be used to determine when to cease delivery of fluid from the pump 70 to the fluid cell (e.g., when to turn the pump 70 "off" to achieve a desired pressure within a fluid cell). Then, a pressure value may be measured from the manifold 72 after delivery of fluid from the pump 70 to a fluid cell when the pump 70 is not delivering fluid to the fluid cell to measure the "actual" pressure of the fluid cell (e.g., unaffected by the pump 70 running or delivering fluid). Although a single pressure sensor 74 is described herein with reference to FIG. 3, it is to be understood that the exemplary systems, apparatus, and methods describe herein may use, or utilize, any number of pressure sensors located in various positions to measure a plurality of redundant or different pressure values during fluid delivery or when fluid delivery has ceased.

Figure 4:
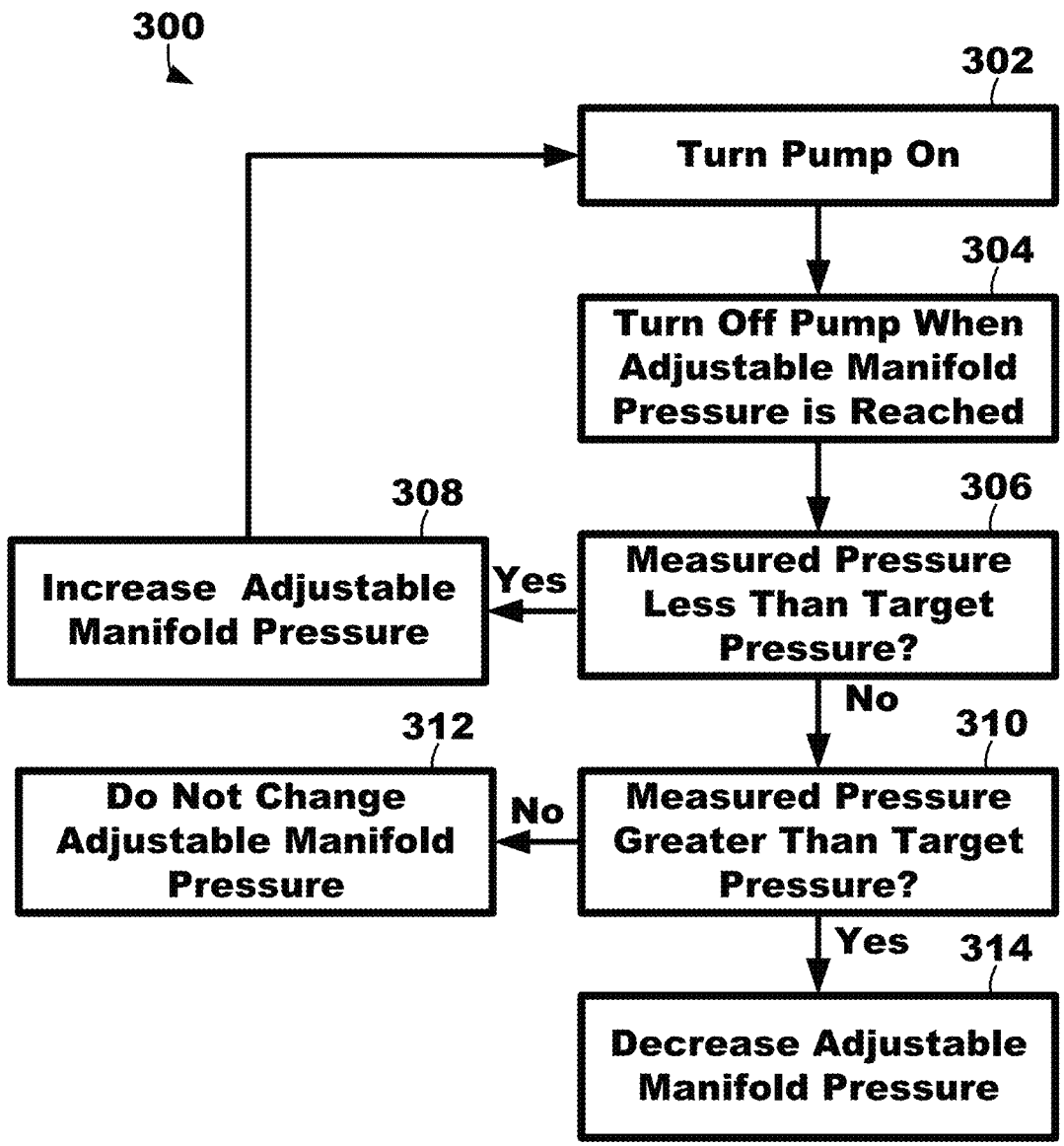
FIG. 4 is a flow chart of an exemplary method of delivering fluid to a fluid cell of a compression garment.

A flow chart of an exemplary method 300 of delivering fluid to a fluid cell of a compression garment is depicted in FIG. 4. Although the exemplary method 300 is described in reference to filling, or providing fluid to, a single fluid cell, it is to be understood that the method 300 could be used for filling, or delivering fluid to, each fluid cell of a plurality of fluid cells of a compression garment such as the compression garments 100, 200 of FIG. 1.

A target pressure and an adjustable manifold pressure may be provided, or used, for each fluid cell of a plurality of fluid cells of a compression garment. The target pressure may be the desired pressure for the fluid cell, and the adjustable manifold pressure may be the pressure value that is used to determine when to cease delivery of fluid from the pump to achieve the target pressure. Additionally, it is to be understood that the target pressure may include a tolerance of, for example, about 5%. In other embodiments, the tolerance may be greater than or equal to about 0.5%, greater than or equal to about 1%, greater than or equal to about 2%, greater than or equal to about 3%, greater than or equal to about 6.5%, etc. and/or less than or equal to about 10%, less than or equal to about 7.5%, less than or equal to about 6%, less than or equal to about 4%, less than or equal to about 3.5%, less than or equal to about 2.5%, etc. Thus, in this example, a measured pressure within a selected percentage of the target pressure would be determined as "meeting" or achieving the target pressure. Furthermore, a measured pressure that is less than the selected percentage of the target pressure would be determined as being less than the target pressure, and conversely, a measured pressure that is greater than the selected percentage of the target pressure would be determined as being greater than the target pressure.

The exemplary method 300 may include "turning" the pump "on" 302 such that fluid is delivered to the manifold, and in turn, to a fluid cell of a compression garment, and "turning" the pump "off" 304 when the pressure in the manifold meets, or reaches, the adjustable manifold pressure. After the pump has ceased delivering fluid to the manifold (e.g., while the pump is "turned off"), the pressure in the manifold may be again measured and compared against, or compared to, the target pressure. If the measured pressure is less than the target pressure 306, then the method 300 may increase the adjustable manifold pressure 308 and return to delivering fluid via the pump by "turning" the pump back "on" 302. As noted herein, the target pressure may have a tolerance of, for example, 5%, and thus, to satisfy process 306, the measured pressure may be less than 5% of the target pressure. Similar to as before, the method 300 may then "turn" the pump "off" 304 when the pressure in the manifold meets, or reaches, the newly-adjustable manifold pressure.

If the pressure measured when the pump is "turned off" is greater than the target pressure 308 (e.g., greater than 5% of the target pressure), then the adjustable manifold pressure may be decreased 314 and filling the fluid cell may be complete. As shown in this embodiment, the method 300 may cease or stop at process 314 and no fluid may be removed from the fluid cell and manifold despite the adjustable manifold pressure being decreased. Instead, the newly-decreased adjustable manifold pressure will be used during the next inflation cycle.

Further, as shown, if the pressure measured when the pump is "turned off" is not greater than the target pressure 308 (e.g., greater than 5% of the target pressure), then the adjustable manifold pressure may not be changed 312 and filling the fluid cell may be complete.

Thus, the method 300 may be described as a learning algorithm or process configured to "learn" the adjustable manifold pressure that may be needed to achieve the target pressure, e.g., within a margin. The adjustable manifold pressure for each fluid cell may be saved by the controller 52 such that, e.g., the adjustable manifold pressure for each fluid cell may be used during future inflation cycles and future therapy sessions.

As described herein, compression garments may include a plurality of fluid cells, each of which may define a different size than each other and may be positioned about a different area or region of a user's body. In some embodiments, one or more of the fluid cells of a single compression garment or multiple compressions garments may include different target pressures. In this way, some fluid cells may be pressurized using the fill method 300 described herein using a target pressure and an adjustable manifold pressure that is different than other fluids cells. Additionally, the adjustable manifold pressure associated each fluid cell of a compression garment may be customized by the method 300.

Further, the rate at which fluid is delivered to fluid cells may be different per compression garment and/or per fluid cell. For example, some fluid cells may utilize a slower fill rate (e.g., the pump may be "run slower" to deliver fluid at a slower rate) than other fluids cells, and some fluid cells may utilize a faster fill rate (e.g., the pump may be "run faster" to deliver fluid at a higher rate) than other fluids cells. Additionally, all fluid cells or a subset of fluid cells of a particular garment may utilize a slower or faster fill rate than all fluid cells or a subset of fluids cells of the same or another garment. For example, a head compression garment may utilize a slower fill rate than other compression garments such as, e.g., a leg compression garment or a trunk compression garment. It may be described that a first rate of fluid delivery may be used for a first compression garment, and a second rate of fluid delivery may be used for a second garment where the first rate is different than the second rate.

Figure 5:
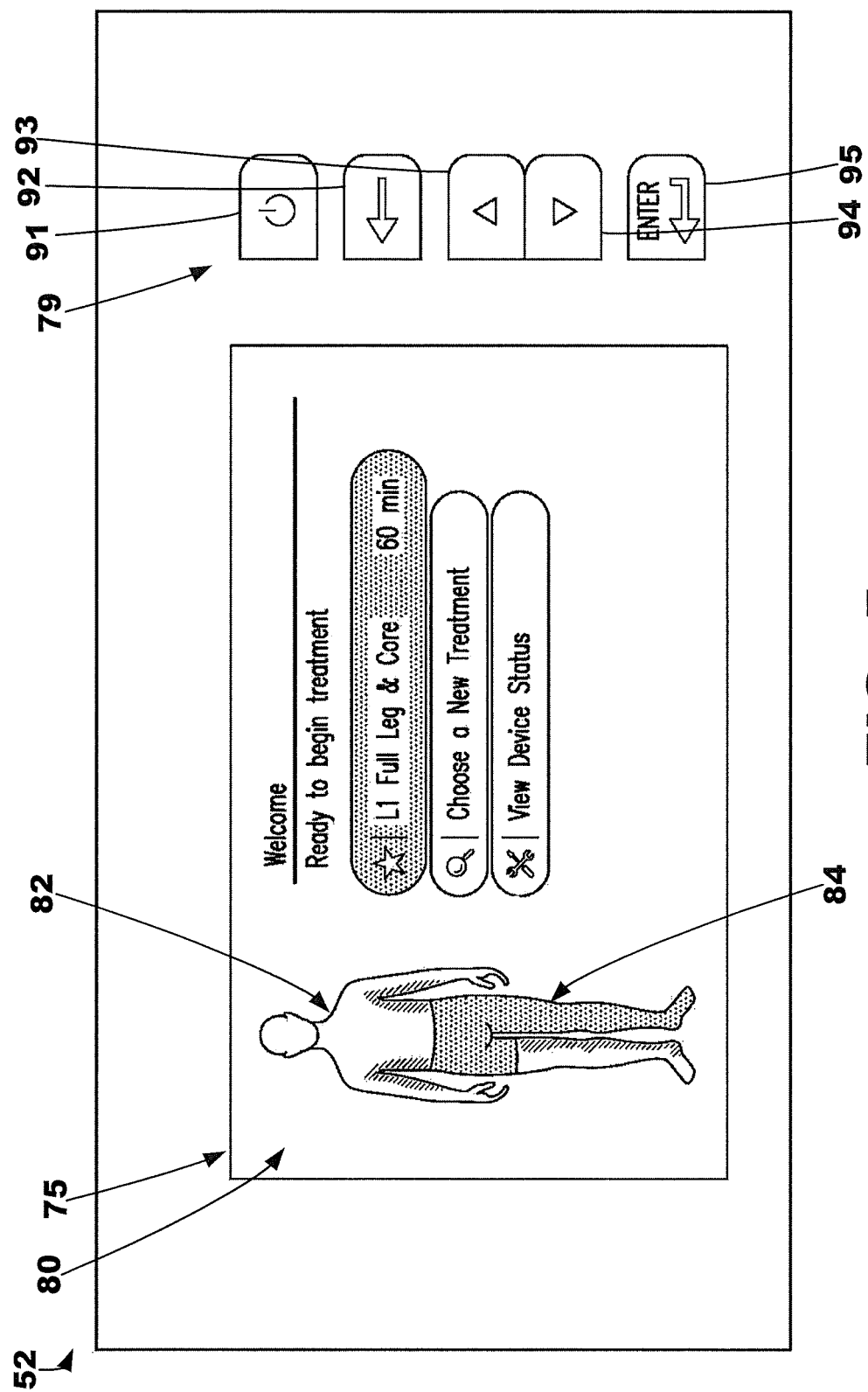
FIG. 5 is front view of a portion of the compression garment controller of FIG. 2 including the graphical user interface.

Various graphical user interfaces and input apparatus may be utilized by the exemplary compression therapy systems and methods described herein. As described herein, a display 75 of a controller 52 may depict a graphical user interface 80 as shown in FIG. 5. The controller 52 may further include input apparatus 79 proximate the graphical user interface 80 and/or display 75 such that, e.g., a user may interact with the graphical user interface 80 to, e.g., configure therapy, "power up" or "turn on" the controller 52, etc. More specifically, the input apparatus 79 may include a power button 91 to "turn on" and "turn off" the controller 52, a "back" button 92 to return to a previously-displayed graphical region, an up menu button 93 to upwardly traverse a menu or plurality of graphical regions, areas, or elements on the graphical user interface 80, a down menu button 94 to downwardly traverse a menu or plurality of graphical regions, areas, or elements on the graphical user interface 80, and an enter button 95 to select an indicated, or highlighted, graphical region, area, or element of the graphical user interface 80.

One exemplary graphical user interface 80 such as shown in FIGS. 5-6 may include, at least, a human-shaped graphical element 82 and a compression therapy graphical indication 84 on the human-shaped graphical element 82 indicative of the location of compression therapy deliverable or being delivered by compression therapy apparatus such as compression garment operably coupled to the controller 52. The human-shaped graphical element 82 may include any graphical depiction that depicts the form of a human. In this example, the human-shaped graphical element 82 is a featureless, shaded outline of standing human. In other embodiments, the human-shaped graphical element 82 may include more or less features than depicted in FIGS. 5-6. For example, the human-shaped graphical element 82 may include colorization, facial features, etc. In one instance, the human-shaped graphical element 82 may be a "stick figure" (which includes single lines representing the torso, legs, arms, neck, and a single-line circle representing the head). In another instance, the human-shaped graphical element 82 may be photograph of a human or patient.

The compression therapy graphical indication 84 may include any graphical depiction that when presented, or displayed, to a user would convey where compression therapy is to be applied or is being applied about the human-shaped graphical element 82. The compression therapy graphical indication 84 may include various colors, animations, outlines, shading, etc. to indicate the compression therapy about the human-shaped graphical element 82.

In this example, the compression therapy graphical indication 84 is a darkened, or shaded, region about the human-shaped graphical element 82. As shown, the darkened, or shaded, region covers the left leg, the lower trunk region, and the upper right leg region of the human-shaped graphical element 82 to indicate that compression therapy of the controller 52 is presently configured for a trunk garment 100 and left leg garment 200 donned about a user's body as shown in FIG. 1. In this way, a user can quickly and easily confirm, or ascertain, which garments the user is to be wearing and/or which therapy is presently configured on the controller 52.

More specifically and as will be shown in the graphical user interface 80 of FIGS. 6-11, the human-shaped graphical element 82 may be described as including, or defining, a plurality of body regions such as, e.g., a left leg, a right leg, a trunk region, a torso or chest region, a left arm region, a right arm region, a chest and left arm region, a chest and right arm region, a neck region, and a head region. The compression therapy graphical indication 84 may be displayed on, or depicted about, at least one body region of such body regions to indicate that compression therapy is deliverable thereto.

Figure 6A:
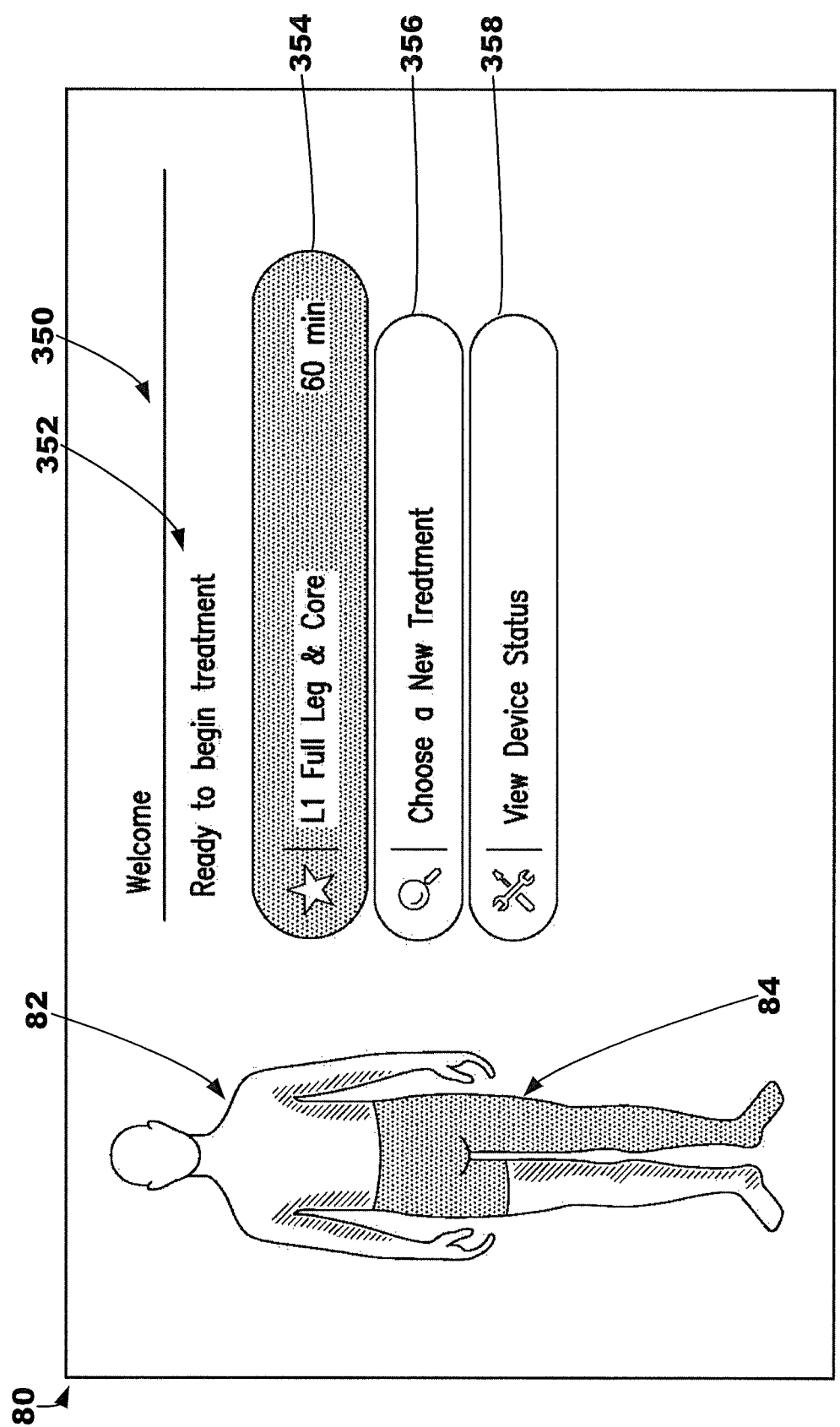
FIGS. 6A-6C is an exemplary graphical user interface of the exemplary system and controller of FIGS. 1-3 and 5 depicting an introduction graphical region.
Figure 6B:
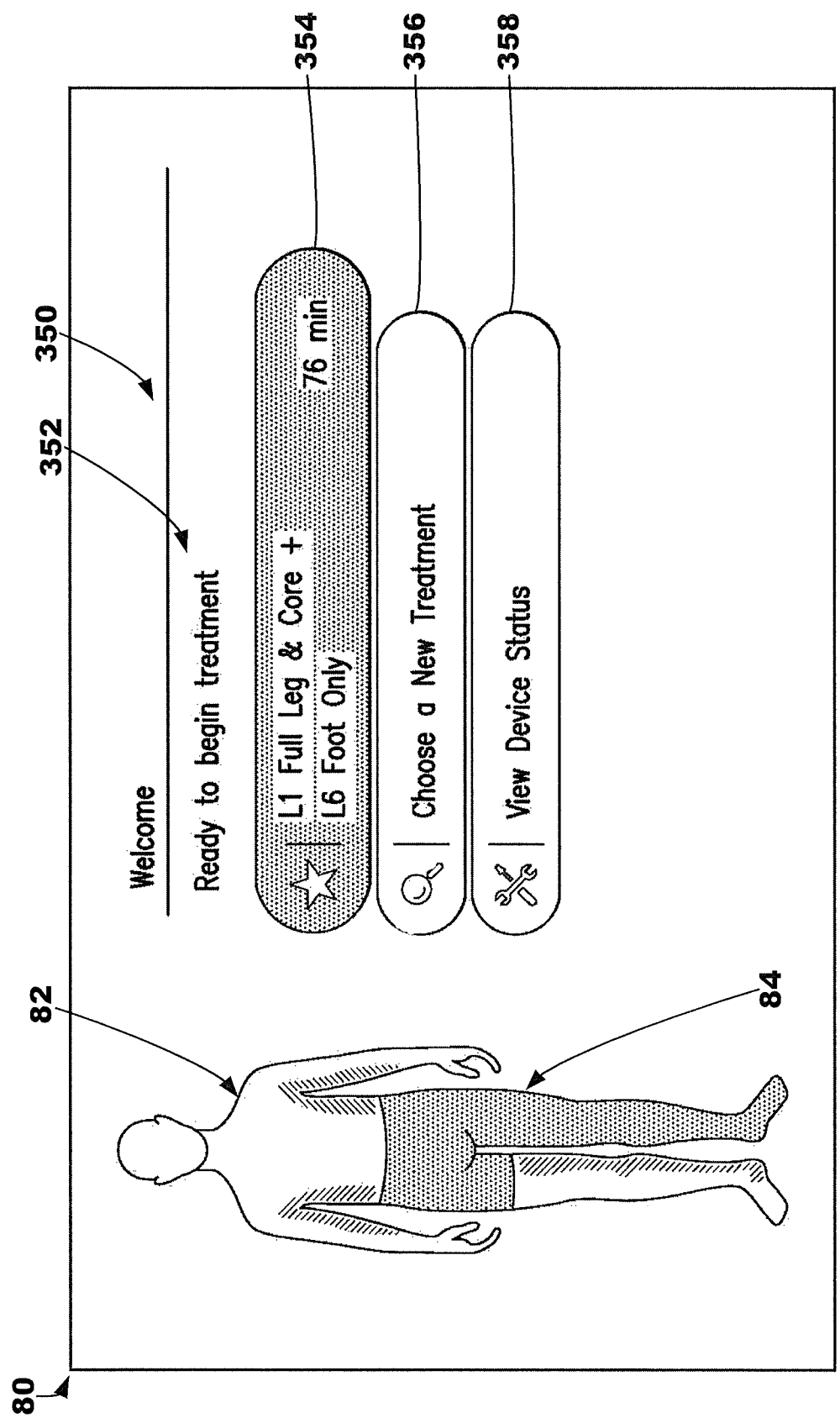
Figure 6C:
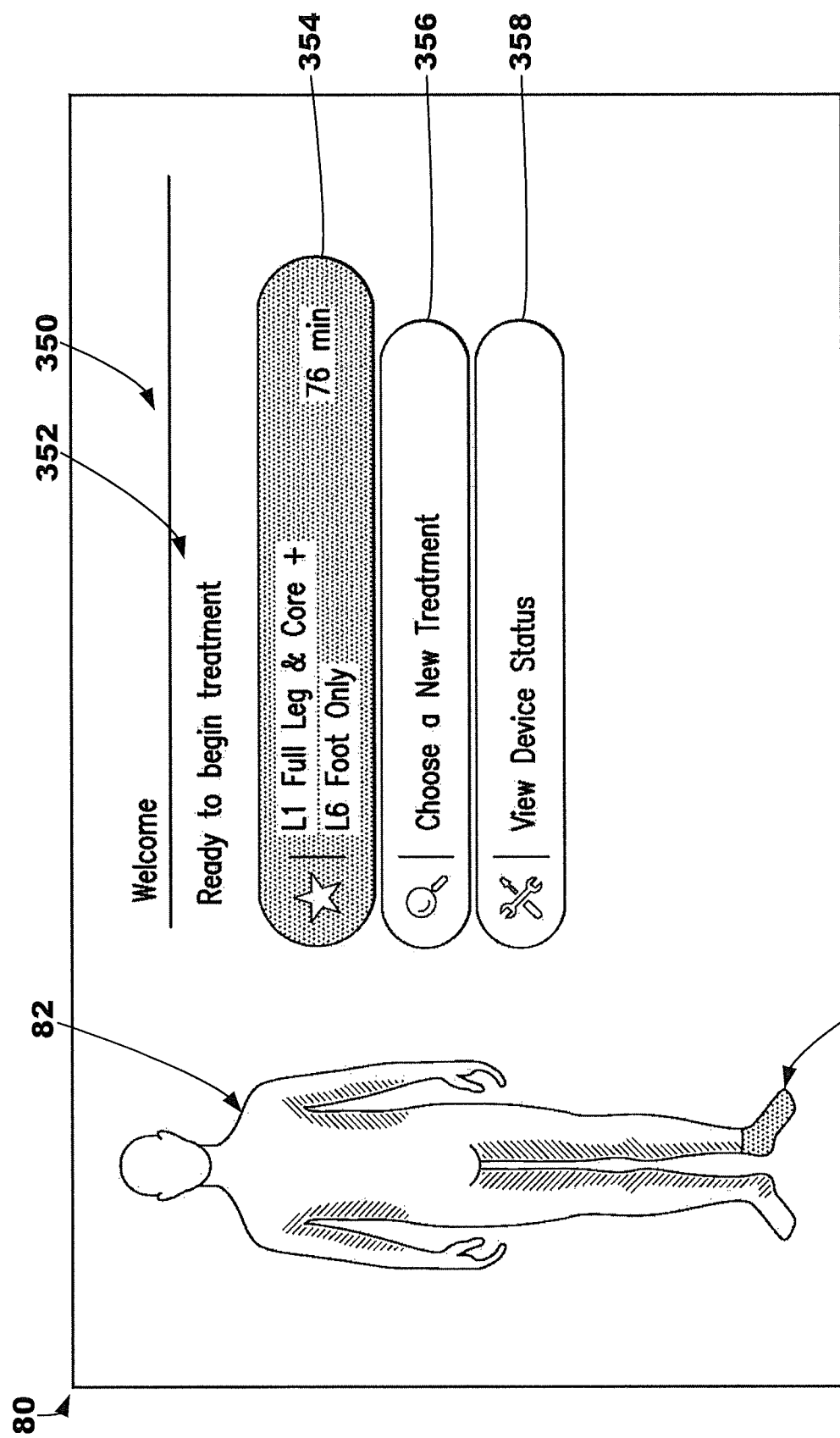

When the controller 52 is "turned on" or "powered up" by a user actuating the button 91, the graphical user interface 80 may display an introduction graphical region 350 as shown in FIGS. 6A-6C. The introduction graphical region 350 may include a status message 352. As depicted in this embodiment, the status message 352 reads "Welcome—Ready to Begin Treatment."

The introduction graphical region 350 depicts three selectable graphical areas: a default therapy graphical area 354, a choose therapy 356 graphical area, and a view device status graphical area 358. Upon selection of the default therapy graphical area 354 (which may be selected using the input apparatus 79, or more specifically, by using the up and down menu buttons 93, 94 to indicate, or highlight, the default therapy graphical area 356 and the enter button 95 to select the default therapy graphical area 354), a default, or saved, compression therapy configuration may be loaded and such compression therapy may begin. Although a single default therapy graphical area 354 is depicted in FIG. 6A, it is to be understood that more than one default therapy graphical areas 354 may be depicted on the introduction graphical region 350 (e.g., depending on how many default or saved compression therapy configurations are stored on the controller). As shown in FIG. 6A, the default therapy graphical area 354 indicates that "L1 Full Leg & Core 60 min" is the default or saved compression therapy, and thus, selection thereof will load and begin such therapy. Further, the compression therapy graphical indication 84 is positioned about the left leg and trunk of the human-shaped graphical element 82 in correspondence with the default or save compression therapy. Thus, a user may quickly visualize what portions of the body the default or saved compression therapy will provide compression therapy thereto. If a user selects the default therapy graphical area 354, the controller 52 may begin such therapy and display the therapy status graphical region 365 of FIG. 7A, which is described later herein.

Upon selection of the choose therapy graphical area 356, a therapy configuration graphical region 380 may be displayed on the graphical user interface 80 as shown and described herein with respect to FIGS. 8-11. Further, upon selection of the view device status graphical area 358, graphical regions depicting information with respect to the device status and configuration may be depicted on the graphical user interface 80 such as, e.g., software version, device status, various self-tests, etc.

Another embodiment of the introduction graphical region 350 is depicted in FIGS. 6B-6C. In this embodiment, the default therapy graphical region 354 indicates that "L1 Full Leg & Core+L6 Foot Only 76 min" is the default or saved compression therapy. Such default or saved compression therapy includes two process or steps of compression therapy: namely, a "L1 Full Leg & Core" compression therapy program and a "L6 Foot Only" compression therapy program, which will be run sequentially (e.g., one-after-another, "back-to-back," etc.). Correspondingly, the compression therapy graphical indication 84 may indicate both of the compression therapy programs by, in this example, "flashing" between the compression therapy graphical indication 84 being positioned about the leg and trunk of the human-shaped graphical element 82 as shown in FIG. 6B and the foot of the human-shaped graphical element 82 as shown in FIG. 6C. In this way, a user may quickly visualize that the default or saved therapy configuration includes two therapy programs: the first providing compression therapy about the user's left leg and trunk; and the second providing compression therapy about the user's left foot. It is to be understood that the compression therapy graphical indication 84 for multiple compression therapy programs being run consecutively as shown in FIGS. 6B-6C is only one embodiment, and other ways of indicating such multiple compression therapy programs being run consecutively are considered by this disclosure. For example, instead of the compression therapy graphical indication 84 "flashing" between the two therapy programs, the compression therapy graphical indication 84 may include two distinguishable indications (e.g., different colors, different shading, different animation, etc.) that may be displayed about the human-shaped graphical element 82.

Figure 7A:
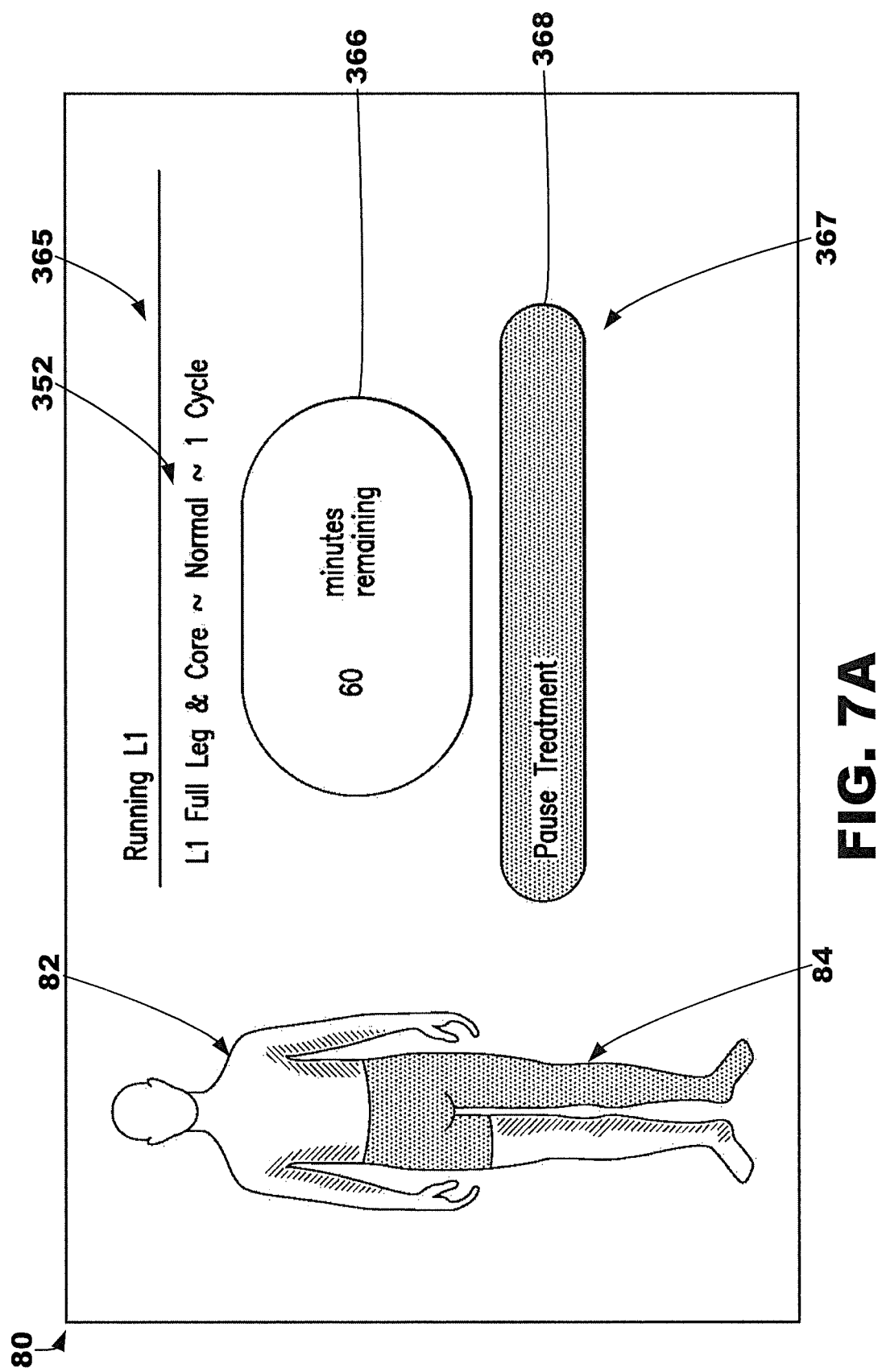
FIGS. 7A-7C is an exemplary graphical user interface of the exemplary system and controller of FIGS. 1-3 and 5 depicting a therapy status graphical region.
Figure 7B:
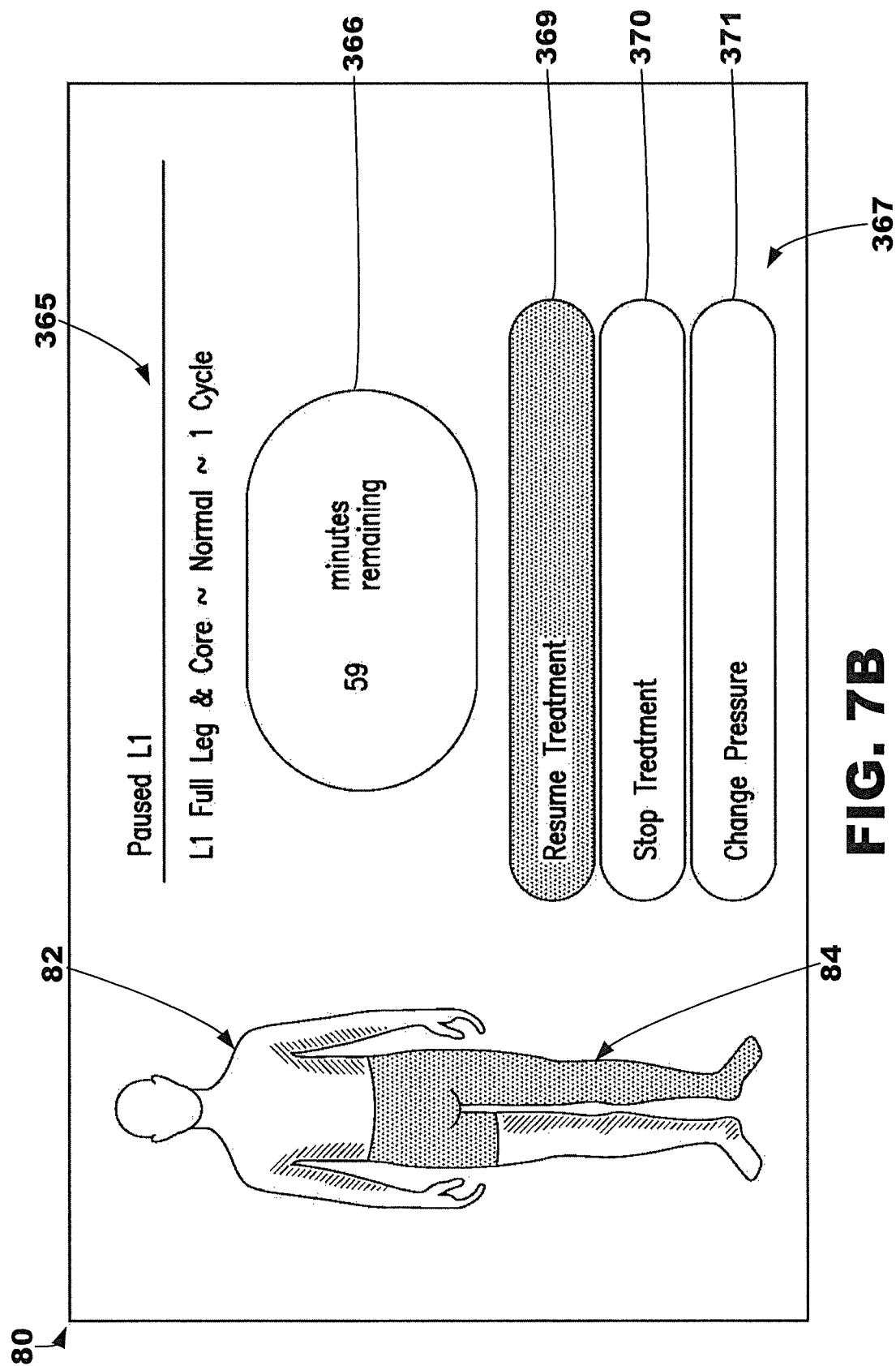
Figure 7C:
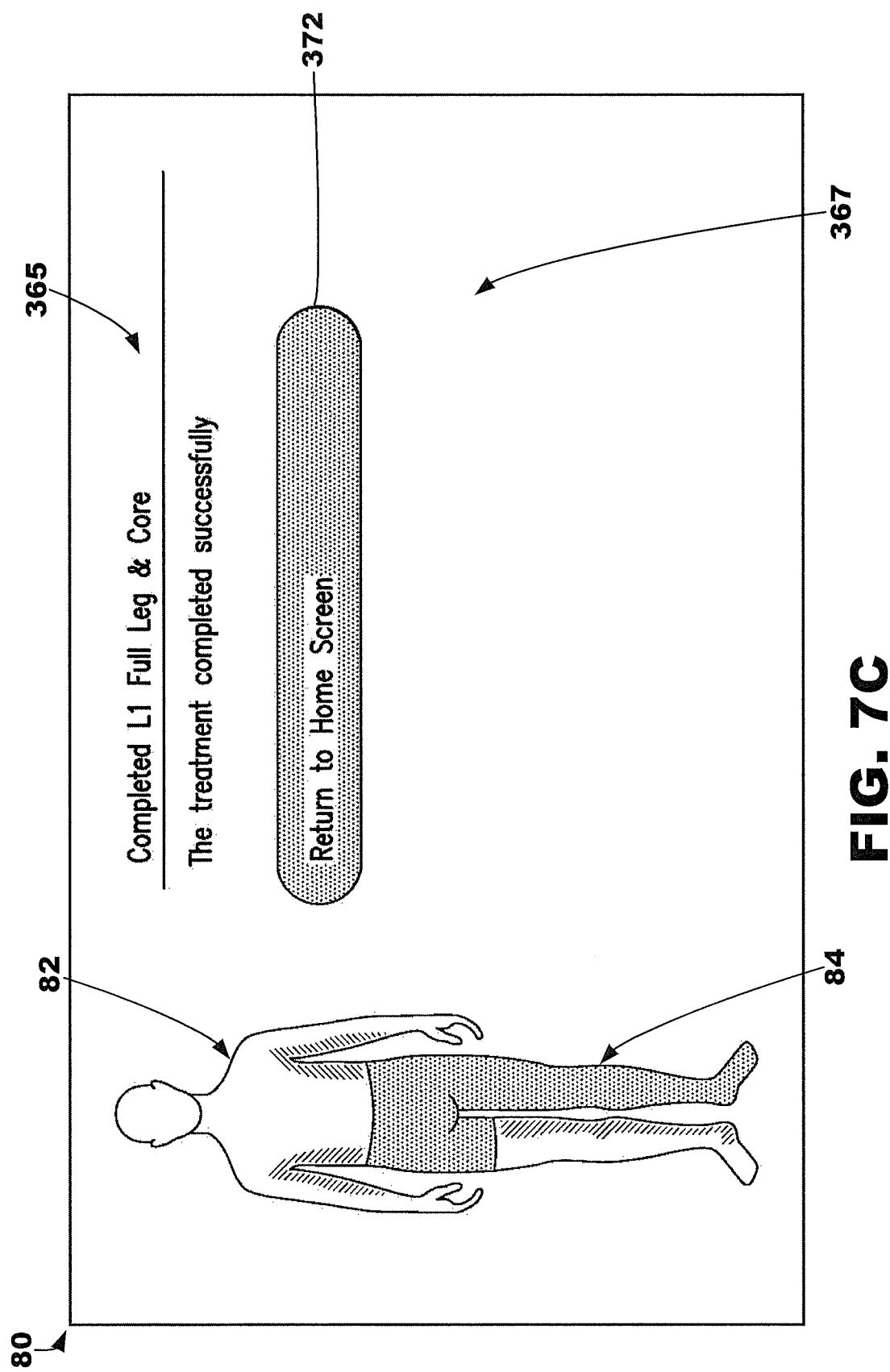

A therapy status graphical region 365 is depicted in FIGS. 7A-7C which is shown on the graphical user interface 80 during execution of a compression therapy program to allow a user to view status information regarding the compression therapy being delivering to the patient. As shown, the graphical user interface 80 still includes, or depicts, the human-shaped graphical element 82 and the compression therapy graphical indication 84 about the human-shaped graphical element 82 indicating where the compression therapy of the ongoing compression therapy program is being delivered or will be delivered. As shown in FIG. 7A, the ongoing compression therapy program is "L1 Full Leg & Core—Normal—1 Cycle," which is recited, or depicted, as a status message 352.

Further, the therapy status region 365 includes a therapy duration area 366 depicting an amount of time remaining for one or more cycles of the compression therapy. As shown, the therapy duration area 366 indicates that 60 minutes is remaining for the compression therapy program to complete.

Additionally, the therapy status graphical region 365 includes an action area 367 to allow a user to pause, stop, resume, or modify the compression therapy being delivered. For example, if a user selects a "Pause" graphical element 368 of the action area 367 as shown in FIG. 7A, the therapy program may be paused (e.g., the pump may stop delivering fluid to fluid cells) and the therapy status graphical region 365 of FIG. 7B may be depicted.

Figure 12B:
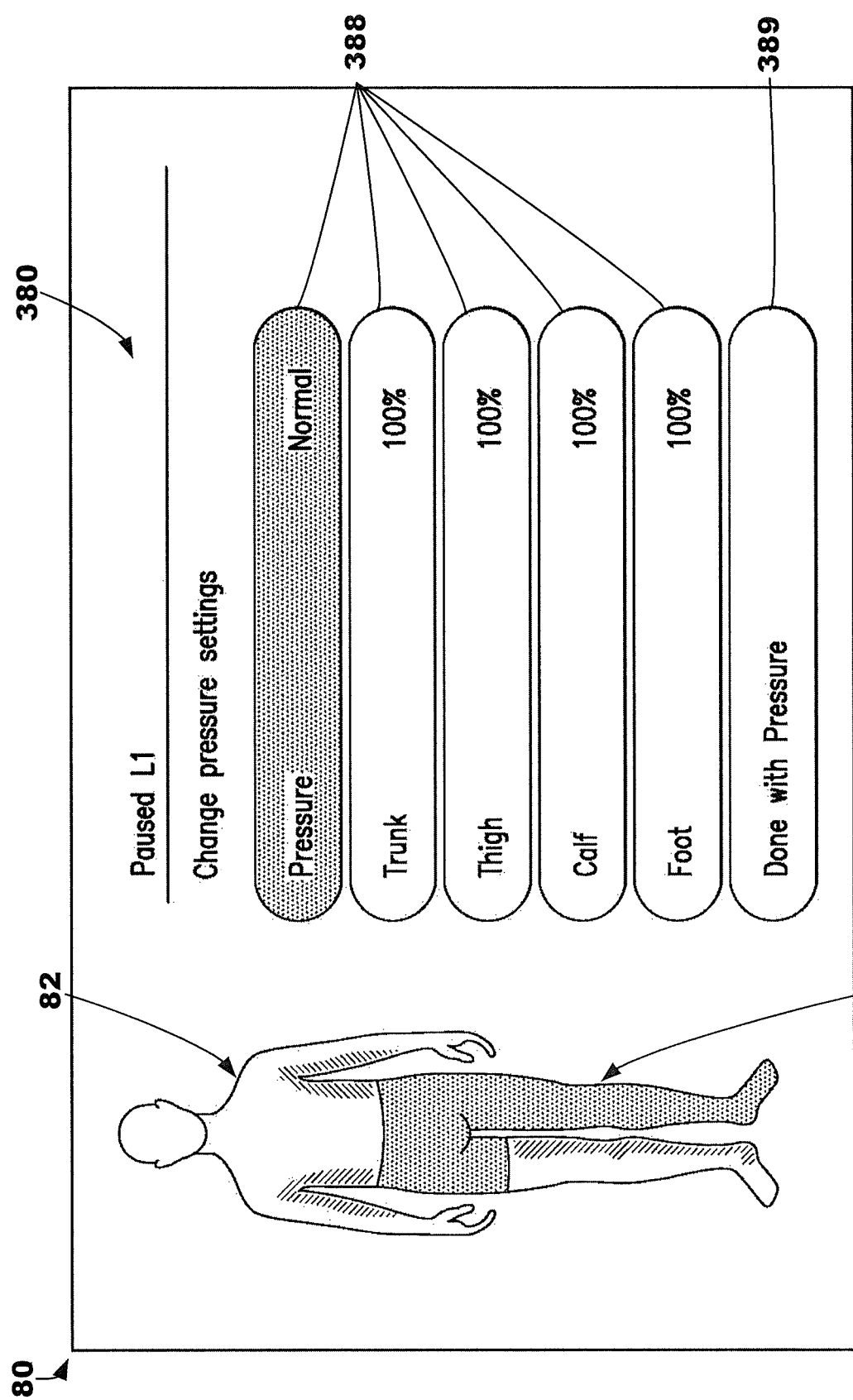
Figure 12C:
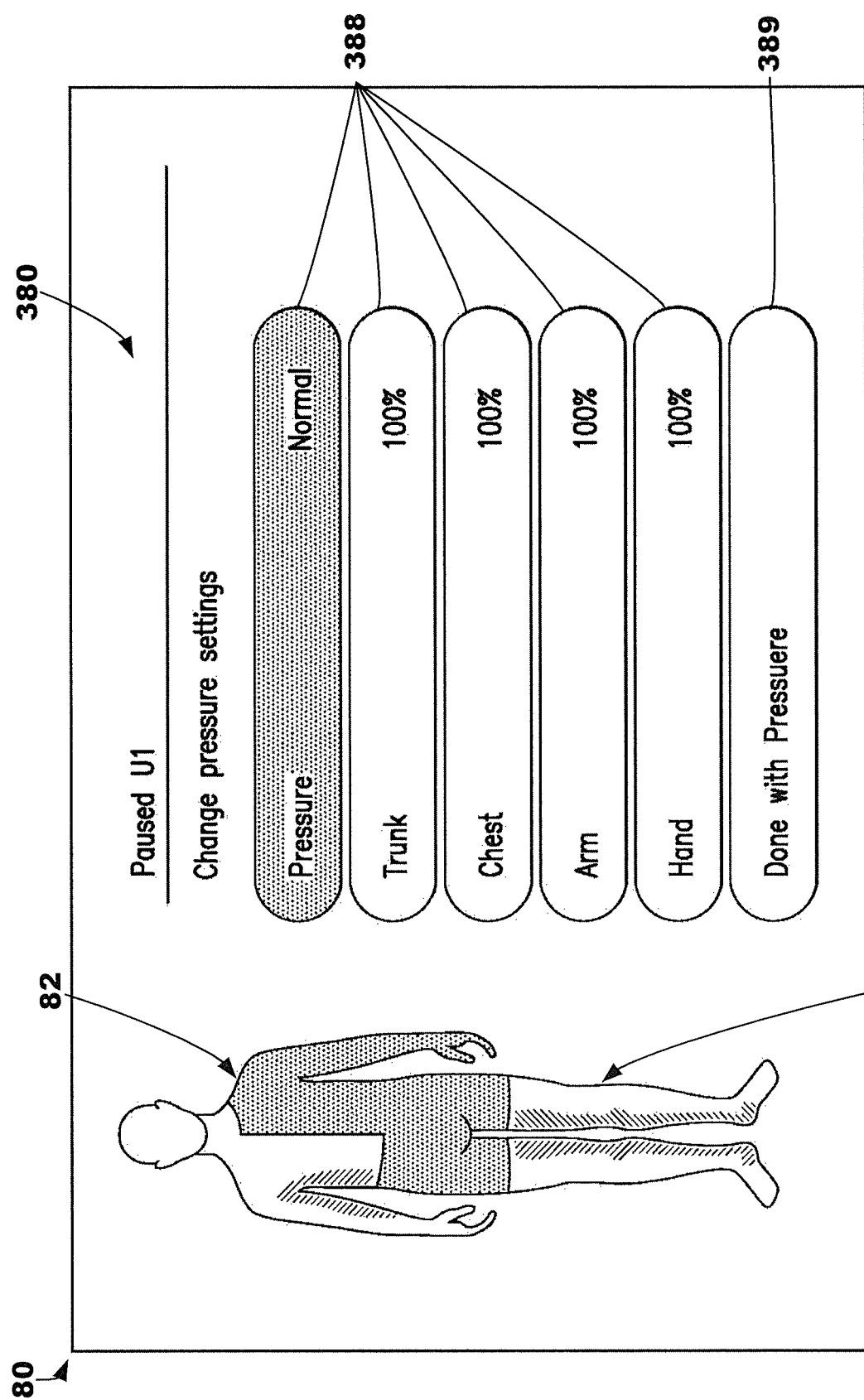

When therapy is paused, the action area 367 of the therapy status graphical region 365 of FIG. 7B may provide multiple options to a user. As shown, three graphical elements are displayed, or depicted, in the action area 367 in FIG. 7B, namely, a "Resume Treatment" graphical element 369 that upon selection will resume the compression therapy program and also return to display of the therapy status graphical region 365 of FIG. 7A on the graphical user interface 80, "Stop Treatment" graphical element 370 that upon selection will cease the compression therapy program and also return to display of the introduction graphical region 350 of FIG. 6A on the graphical user interface 80, and a "Change Pressure" graphical element 371 that upon selection will allow a user to change the pressure of the current compression therapy program similar to as shown in FIGS. 12A-12C, which is described later herein.

Once the compression therapy program completes, the therapy status graphical region 365 may depict a "Return to Home Screen" graphical element 372 in the action area 367 as shown in FIG. 7C, that upon selection will return a user to the introduction graphical region of FIG. 6A.

A therapy configuration graphical region 380 may be displayed on the graphical user interface 80 as shown FIGS. 8-11 to allow a user to configure the compression therapy, and more specifically, a compression therapy program, to be delivered to a user. Generally, it may be described that the therapy configuration graphical region 380 allows a user to select which one or more body regions and which body areas of the selected body regions to deliver therapy thereto as well as allowing configuration of various compression therapy settings.

Figure 8:
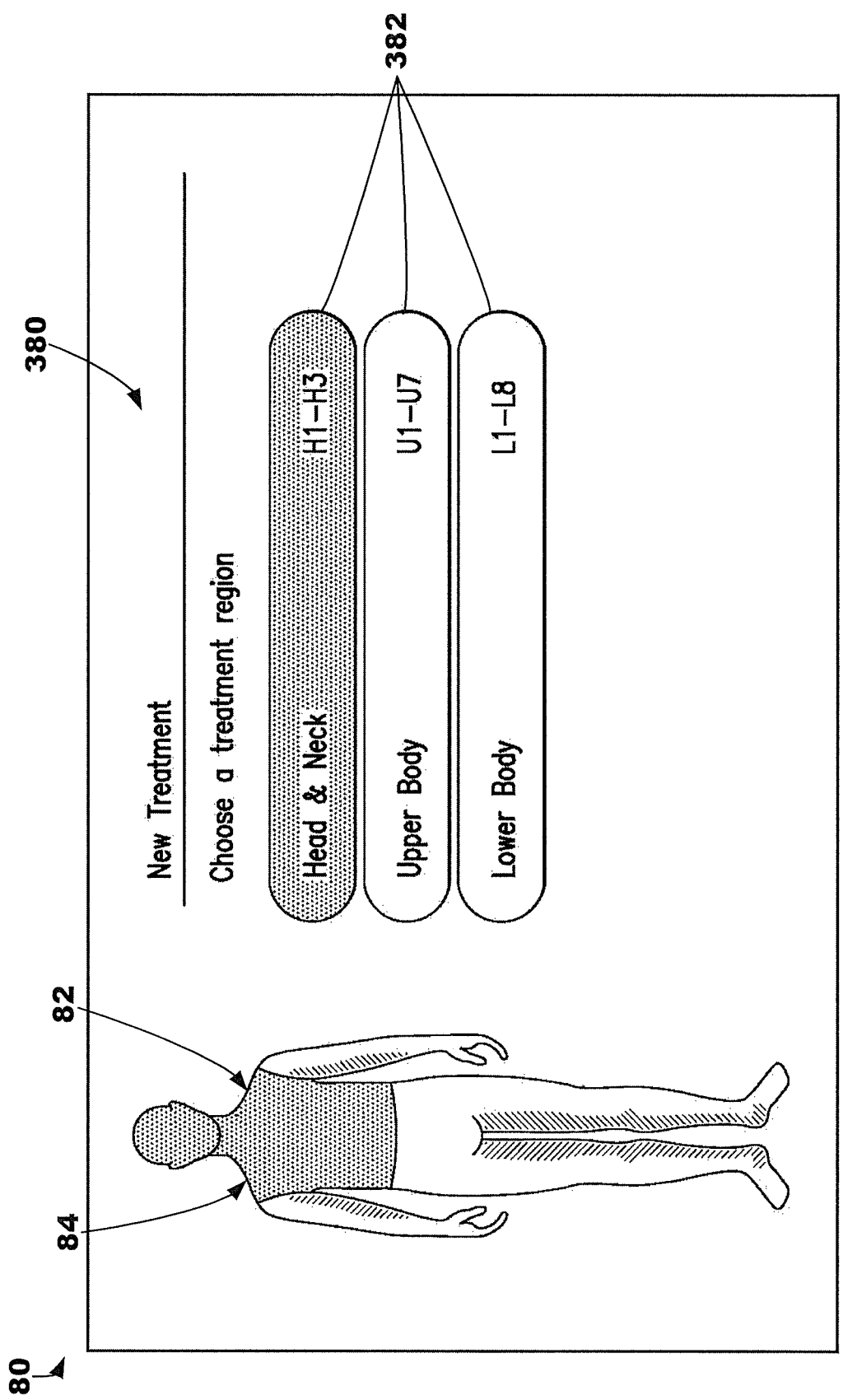
FIG. 8 is an exemplary graphical user interface of the exemplary system and controller of FIGS. 1-3 and 5 depicting a therapy configuration graphical region including selection of a body region.
Figure 9:
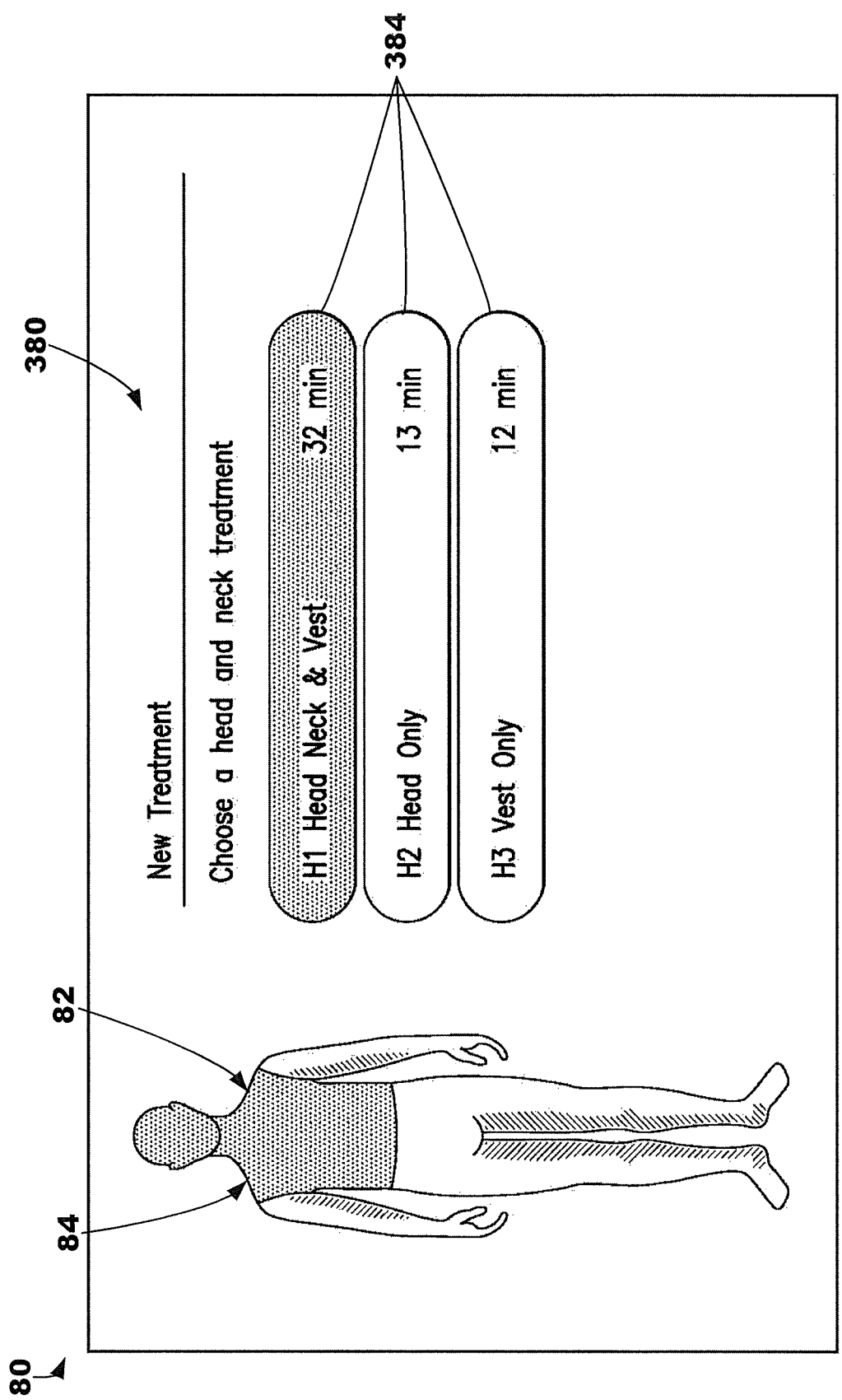
FIGS. 9-10 are exemplary graphical user interfaces of the exemplary system and controller of FIGS. 1-3 and 5 depicting different therapy configuration graphical regions including selection of one or more body areas of a selected body region.
Figure 10:
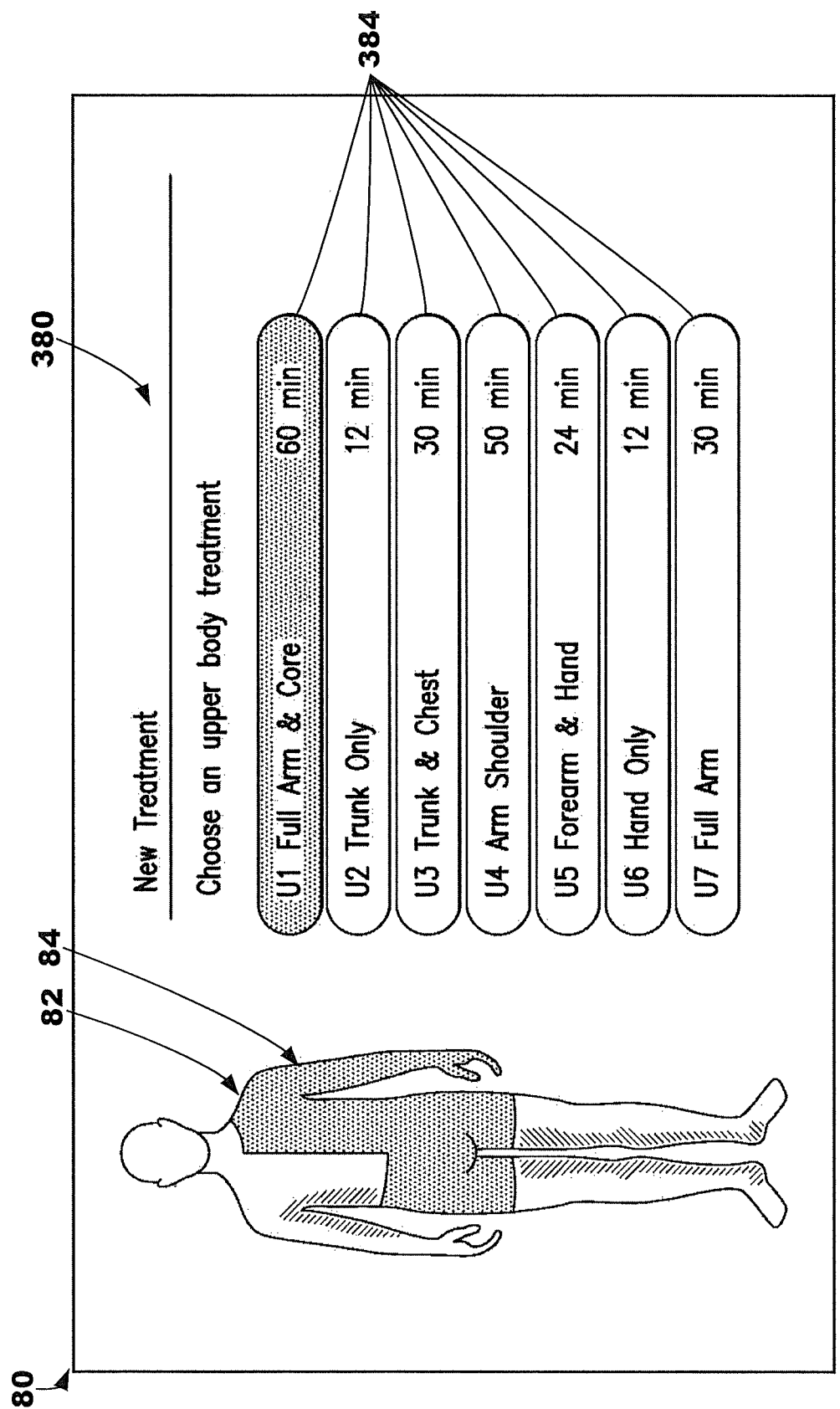

As shown in FIG. 8, the therapy configuration graphical region 380 includes a plurality of selectable treatment regions 382 selectable by a user to select which one or more body regions of the patient to deliver compression therapy to. The therapy configuration graphical region 380 includes, or depicts, a "Head and Neck H1-H3" treatment region 382, an "Upper Body U1-U7" treatment region 382, and a "Lower Body L1-L8" treatment region 382. Selection of one of the treatment regions 382 will initiate configuration of a compression therapy program for the selected treatment region. For example, selection of the "Head and Neck H1-H3" treatment region 382 will initiate configuration of a head and neck compression therapy program as shown in FIG. 9. Further, for example, selection of the "Upper Body U1-U7" treatment region 382 will initiate configuration of an upper body compression therapy program as shown in FIG. 10. And still further, for example, selection of the "Lower Body L1-L8" treatment region 382 will initiate configuration of a lower body compression therapy program as shown in FIGS. 11A-11F.

Further, as shown, the human-shaped graphical element 82 and the compression therapy graphical indication 84 depicted about the human-shaped graphical element 82 are also displayed on the graphical user interface 80 in conjunction with the therapy configuration graphical region 380. Thus, when a user indicates, or highlights, one of the selectable treatment regions 382 prior to selection thereof (e.g., using the up and down menu buttons 93, 94 to indicate, or highlight, the desired treatment region 382), the compression therapy graphical indication 84 will correspond to the indicated, or highlighted, treatment region 382. For example, as shown in FIG. 8, the "Head and Neck H1-H3" treatment region 382 is indicated (e.g., shaded darker than the other treatment regions 382), and thus, the compression therapy graphical indication 84 is depicted about the torso and head of the human-shaped graphical element 82 indicating that the compression therapy programs for the head and neck provide compression therapy to the torso and/or head of the user. Likewise, if a user indicated or highlighted a different treatment region 382, the compression therapy graphical indication 84 would reflect the indicated or highlighted treatment region 382 accordingly so as to indicate the body regions where compression therapy would or could be applied for such treatment region.

The therapy configuration region 380 after selection of the "Head and Neck H1-H3" treatment region 382 is depicted in FIG. 9. As shown, a plurality of selectable treatment areas 384 are depicted on the therapy configuration region 380 that are selectable by a user to select one or more body areas of the patient to deliver compression therapy thereto. Such body areas are a subset of the selected body portions. For example, since the "Head and Neck H1-H3" treatment region 382 was selected in FIG. 8, the selectable treatment areas 384 include "H1 Head Neck & Vest," "H2 Head Only," and "H3 Vest Only," "H2 Head Only," and "H3 Vest Only," each of which are configured to provide head and neck compression therapy.

Each of the selectable treatment areas 384 includes, or depicts, a time period or duration associated therewith, which is the period of time of the compression therapy programs associated with the selectable treatment areas 384. As shown, the compression therapy program associated with the "H1 Head Neck & Vest" treatment area 384 has a duration of 32 minutes, the compression therapy program associated with the "H2 Head Only" treatment area 384 has a duration of 13 minutes, and the compression therapy program associated with the "H3 Vest Only" treatment area 384 has a duration of 12 minutes.

The therapy configuration region 380 after selection of the "Upper Body U1-U7" treatment region 382 is depicted in FIG. 10. As shown, a plurality of selectable treatment areas 384 are depicted on the therapy configuration region 380 that are selectable by a user to select one or more body areas of the patient to deliver compression therapy thereto. Since the "Upper body" treatment region 382 was selected in FIG. 8, the selectable treatment areas 384 include "U1 Full Arm & Core," "U2 Trunk Only," "U3 Trunk & Chest," "U4 Arm Shoulder," "U5 Forearm & Hand," "U6 Hand Only," and "U7 Full Arm," each of which are configured to provide upper body compression therapy. Further, similar to the therapy configuration region 380 of FIG. 9 with respect to head and neck therapy, each of the selectable treatment areas 384 includes, or depicts, a time period or duration associated therewith and the compression therapy graphical indication 84 about the human-shaped graphical element 82 will shift depending on the indicated or highlighted treatment area 384.

Figure 11A:
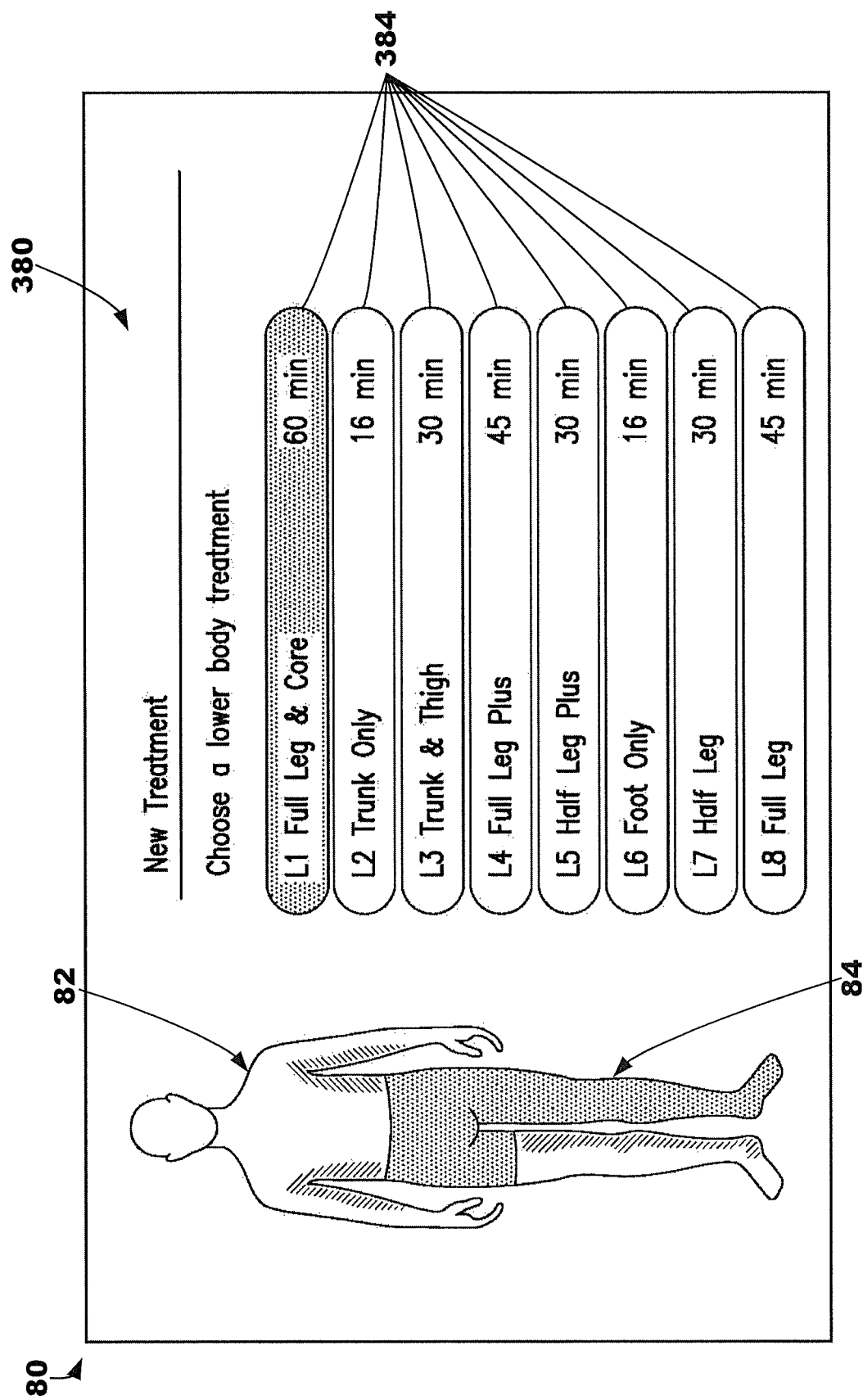

The therapy configuration region 380 after selection of the "Lower Body" treatment region 382 is depicted in FIG. 11A. As shown, a plurality of selectable treatment areas 384 are depicted on the therapy configuration region 380 that are selectable by a user to select one or more body areas of the patient to deliver compression therapy thereto. Since the "Lower body" treatment region 382 was selected in FIG. 8, the selectable treatment areas 384 include "L1 Full Leg & Core," "L2 Trunk Only," "L3 Trunk & Thigh," "L4 Full Leg Plus," "L5 Half Leg Plus," "L6 Foot Only," L7 Half Leg," and "L8 Full Leg," each of which are configured to provide lower body compression therapy. Further, similar to the therapy configuration regions 380 of FIGS. 9-10 with respect to head and neck therapy and upper body therapy, each of the selectable treatment areas 384 includes, or depicts, a time period or duration associated therewith and the compression therapy graphical indication 84 about the human-shaped graphical element 82 will shift depending on the indicated or highlighted treatment area 384.

Figure 11B:
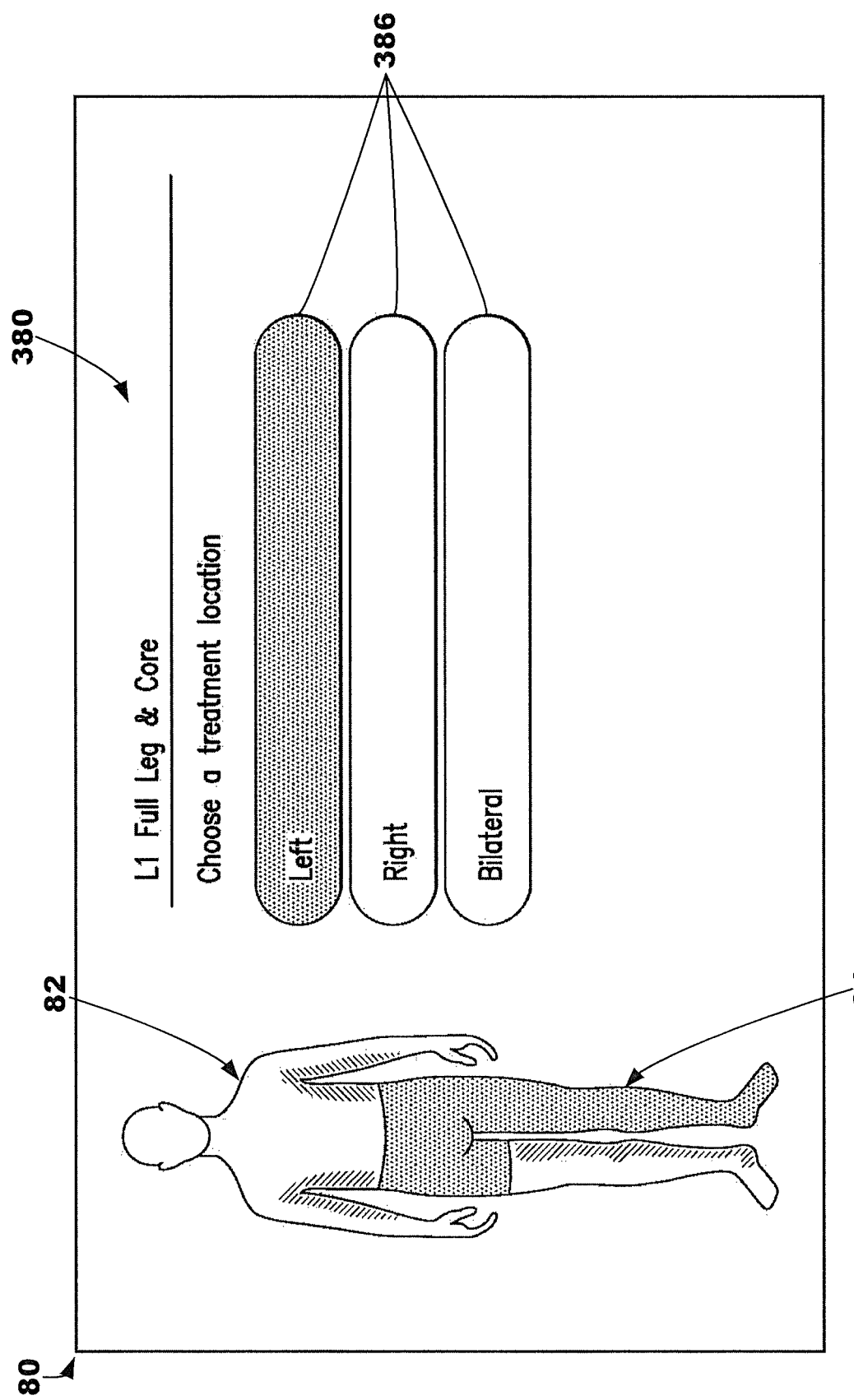
Figure 11D:
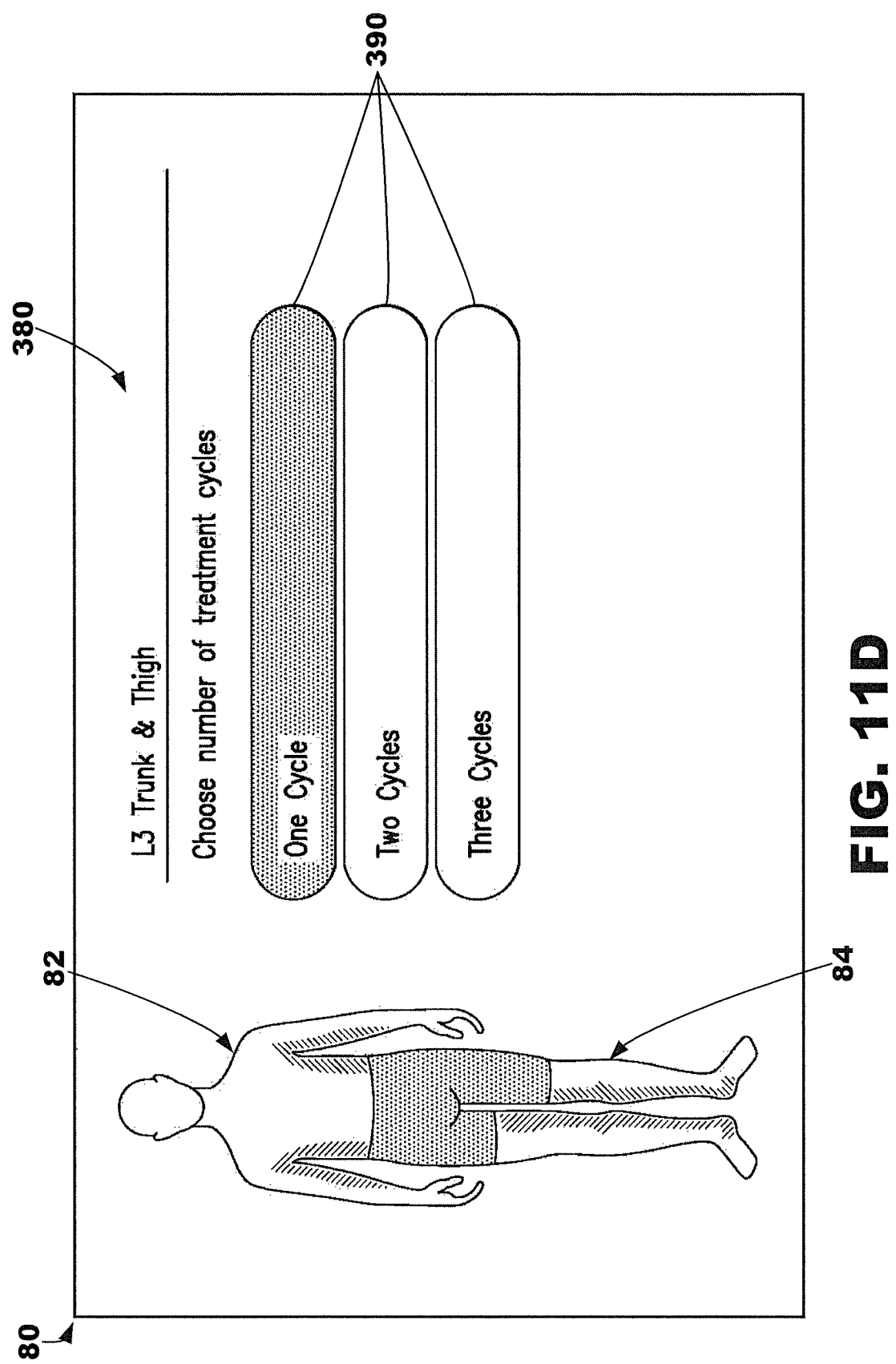

After selection of the "L1 Full Leg & Core," treatment area 384, the therapy configuration region 380 may depict a plurality of treatment locations 386, which may be further subset of the select treatment area as shown in FIG. 11B. More specifically, as shown, a "Left" treatment location 386 that provides compression therapy to the left leg, a "Right" treatment location 386 that provides compression therapy to the right leg, and a "Bilateral" treatment location 386 that provides compression therapy to both legs is depicted in the therapy configuration region 380.

The therapy configuration region 380 may further depict a plurality of treatment pressure variation regions 388 that are selectable by a user to increase, decrease, or maintain the pressure of the compression therapy as depicted in FIG. 11C. Each treatment pressure variation regions 388 may increase or decrease the default or previously-used pressures by a selected amount such as, e.g., a selected percentage such as about 1%, about 2%, about 4%, about 5%, about 7%, about 10%, about 15%, etc. Additionally, limits may be in place such that a user cannot increase or decrease the treatment pressure beyond an upper or lower limit. Further, the therapy configuration region 380 may further depict a plurality of treatment cycle regions 390 selectable by a user to select an amount of cycles of the compression therapy.

Figure 11E:
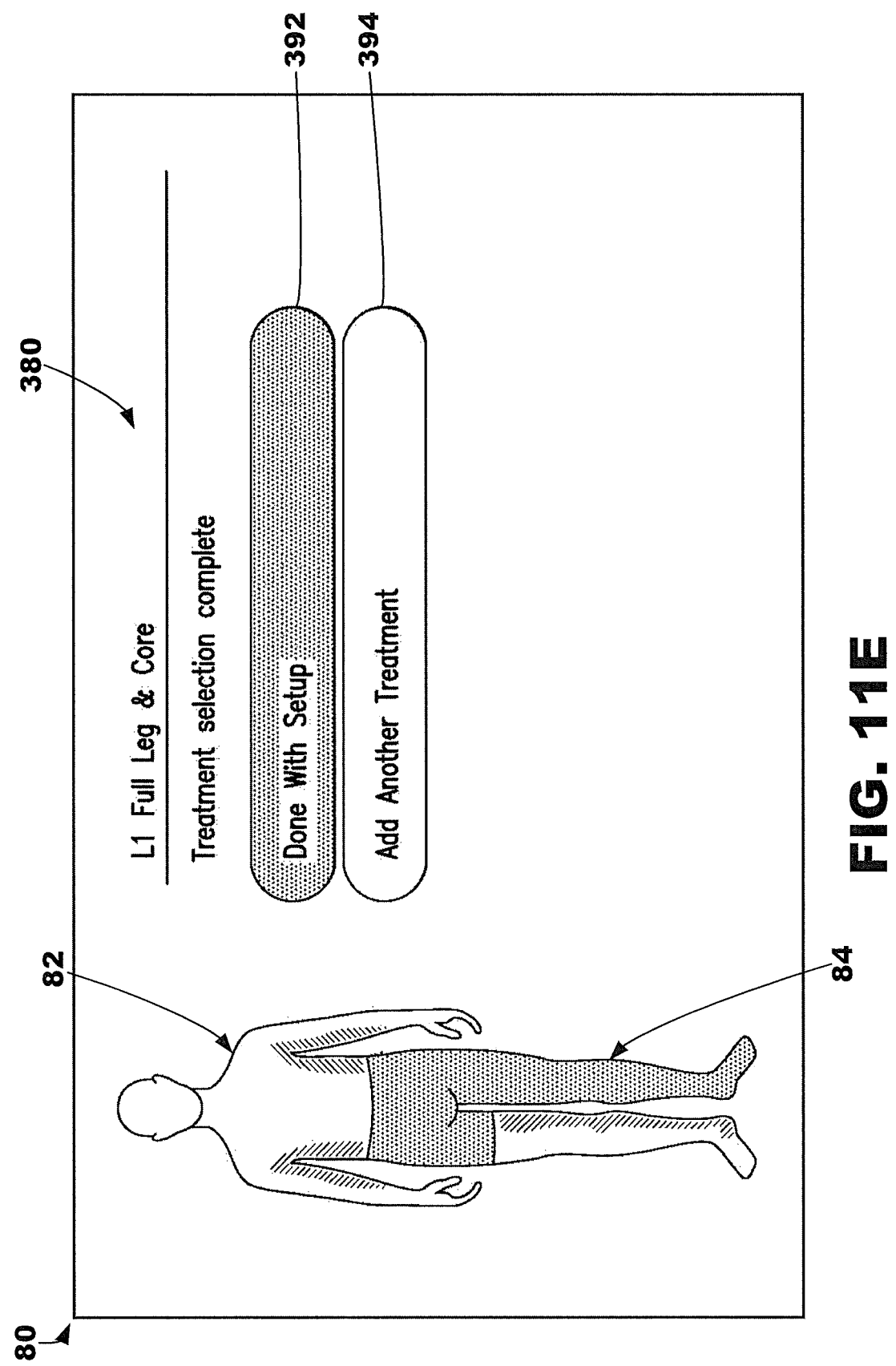

Upon completion of configuration of a compression therapy program, the therapy configuration region 380 may depict, as shown in FIG. 11E, a setup complete selectable graphical region 392 and an add another treatment selectable graphical region 394. Upon selection of the add another treatment selectable graphical region 394, the therapy configuration region 380 of FIG. 8 may be depicted thereby allowing a user to begin the configuration of another compression therapy that may be sequentially performed following the presently-configured compression therapy.

In at least one embodiment, upon selection of the setup complete selectable graphical region 392, the therapy configuration region 380 may depict a plurality of save graphical regions 396 as shown in FIG. 11F that, upon selection, allow a user to save the presently-configured compression therapy such that is displayed on the introduction graphical region 350 as shown in FIGS. 6A-6C. In other words, users may save one or more preset, or default, compression therapies that may be easily accessible and retrievable at a later time.

In at least one embodiment, a controller 52 may include a default compression therapy program that is preset for a particular user such that, when the user first receives the controller 52, a default compression therapy program is already preset for them and "ready to go." In at least one embodiment, such default compression therapy program may not be able to be deleted or removed from the controller 52. In this embodiment, a default compression therapy program may be distinguished from a saved compression therapy program (e.g., saved using the save graphical regions 396) since a saved compression therapy program may be removed and/or overwritten while a default compression therapy program may not be removed or overwritten. In at least one embodiment, the default compression therapy program may follow a prescription prescribed by a user's doctor.

In at least another embodiment, upon selection of the setup complete selectable graphical region 392, the compression therapy may begin and the therapy status graphical region 365 similar as shown in FIG. 7A may be depicted on the graphical user interface 80.

Another embodiment of a therapy configuration region 380 depicting a plurality of treatment pressure variation regions 388 that are selectable by a user to set a pressure therapy program as depicted in FIGS. 12A-12C. For example, the pressure for the current therapy program may be changed between decreased, normal, and increased (e.g., as shown in FIGS. 12A-12C the pressure is set as "Normal") such that an initial pressure may be set for each of the components thereof (e.g., a base setting). In one or more embodiments, the base pressure setting may be described as decreasing, maintaining, or increasing the default or previously-used pressures by a selected amount (e.g., a selected percentage of about 1%, about 2%, about 4%, about 5%, about 7%, about 10%, about 15%, etc.). Additionally, each pressure variation region 388 (e.g., vest, head, trunk, thigh, calf, foot, chest, arm, hand, etc.) may be adjusted independently between, for example, 25%, 50%, 75%, and 100% of the set base pressure setting. In other words, each separate component may be individually and independently altered from the base setting. Furthermore, after each treatment pressure variation region 388 is set, the user may select region 389 to indicate the completion of pressure adjustment.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g., 1 to 5 includes 1, 1.5, 2, 2.75, 3, 3.80, 4, and 5) and any range within that range.

Particular materials and dimensions thereof recited in the disclosed examples, as well as other conditions and details, should not be construed to unduly limit this disclosure. Although the subject matter has been described in language specific to structural features and/or methodological acts, it is to be understood that the subject matter defined in the appended claims is not necessarily limited to the specific features or acts described above. Rather, the specific features and acts described above are disclosed as representative forms of implementing the claims.

What is claimed:

1. A compression garment system comprising:
a compression therapy apparatus operably couplable to a compression garment to provide compression therapy to a patient;
a display comprising a graphical user interface to display information related to the compression therapy;
a communication interface comprising an antenna to communicate with the compression garment; and
a controller comprising one or more processors and operably coupled to the compression therapy apparatus and the communication interface, the controller configured to:
communicate with the compression garment using the communication interface;
identify the compression garment based on the communication with the compression garment using the communication interface; and
configure compression therapy to be delivered by the compression garment based on the identity of the compression garment.

2. The compression garment system of claim 1, wherein identifying the compression garment using the communication interface comprises identifying the compression garment using radiofrequency identification (RFID).

3. The compression garment system of claim 1, wherein identifying the compression garment using the communication interface comprising identifying the compression garment using Bluetooth.

4. The compression garment system of claim 1, wherein the controller is further configured to execute:
allowing a user to configure the compression therapy using a user interface device; and
receiving the compression therapy configuration using the communication interface from the user interface device.

5. The compression garment system of claim 1, wherein the controller is further configured to execute transmitting a therapy status information to a user interface device so that the therapy status information is displayable on a graphical user interface of the user interface device.

6. The compression garment system of claim 5, wherein the therapy status information comprises:
a therapy duration area depicting an amount of time remaining for one or more cycles of the compression therapy; and
a pause/resume area to allow a user to pause or resume the compression therapy being delivered.

7. A method for use with compression therapy apparatus including a compression garment:
communicating with the compression garment using a communication interface comprising an antenna;
identifying the compression garment based on the communication with the compression garment using the communication interface; and
configuring compression therapy to be delivered by the compression garment based on the identity of the compression garment.

8. The method of claim 7, wherein identifying the compression garment using the communication interface comprises identifying the compression garment using radiofrequency identification (RFID).

9. The method of claim 7, wherein identifying the compression garment using the communication interface comprising identifying the compression garment using Bluetooth.

10. The method of claim 7, wherein the method further comprises:
allowing a user to configure the compression therapy using a user interface device; and
receiving the compression therapy configuration using the communication interface from the user interface device.

11. The method of claim 7, wherein the method further comprises transmitting a therapy status information to a user interface device so that the therapy status information is displayable on a graphical user interface of the user interface device.

12. The method of claim 11, wherein the therapy status information comprises:
a therapy duration area depicting an amount of time remaining for one or more cycles of the compression therapy; and
a pause/resume area to allow a user to pause or resume the compression therapy being delivered.

13. A compression garment system comprising:
a compression therapy apparatus operably couplable to a compression garment to provide compression therapy to a patient;
a display comprising a graphical user interface to display information related to the compression therapy;
a communication interface comprising an antenna to communicate with a user interface device; and
a controller comprising one or more processors and operably coupled to the compression therapy apparatus and the communication interface, the controller configured to:
receive, using the communication interface, an instruction from the user interface device, wherein the instruction comprises an identity of the compression garment; and
configure compression therapy to be delivered by the compression garment based on the identity of the compression garment.

14. The compression garment system of claim 13, wherein the controller is further configured to transmit therapy status information to the user interface device so that the therapy status information is displayable on a graphical user interface of the user interface device.

15. The compression garment system of claim 14, wherein the therapy status information comprises:
a therapy duration area depicting an amount of time remaining for one or more cycles of the compression therapy; and
a pause/resume area to allow a user to pause or resume the compression therapy being delivered.

16. The compression garment system of claim 13, wherein a therapy configuration graphical region is displayable on the graphical user interface of the user interface device.

17. The compression garment system of claim 16, wherein a human-shaped graphical element and a therapy compression graphical indication is displayable with the therapy configuration graphical region on the graphical user interface of the user interface device.

* * * * *